(12) United States Patent
Blott et al.

(10) Patent No.: US 9,526,817 B2
(45) Date of Patent: Dec. 27, 2016

(54) WOUND CLEANSING APPARATUS WITH STRESS

(71) Applicant: SMITH & NEPHEW PLC, London (GB)

(72) Inventors: Patrick Lewis Blott, York (GB); Bryan Greener, York (GB); Edward Yerbury Hartwell, Hull (GB); Julian Lee-Webb, York (GB); Derek Nicolini, Hull (GB); Clare Green, Crockey Hill (GB); Robin Paul Martin, York (GB)

(73) Assignee: Smith & Nephew PLC, London (GB)

( * ) Notice: Subject to any disclaimer, the term of this patent is extended or adjusted under 35 U.S.C. 154(b) by 68 days.

(21) Appl. No.: 14/184,643

(22) Filed: Feb. 19, 2014

(65) Prior Publication Data

US 2014/0257211 A1    Sep. 11, 2014

Related U.S. Application Data

(60) Division of application No. 12/832,002, filed on Jul. 7, 2010, which is a division of application No.
(Continued)

(30) Foreign Application Priority Data

Apr. 27, 2004  (GB) .................................. 0409291.2

(51) Int. Cl.
*A61M 35/00*   (2006.01)
*A61M 1/00*    (2006.01)
(Continued)

(52) U.S. Cl.
CPC ........ *A61M 1/0037* (2013.01); *A61F 13/0216* (2013.01); *A61M 1/0088* (2013.01);
(Continued)

(58) Field of Classification Search
CPC .......... A61M 35/00; A61M 1/00; A61F 13/00; A61F 13/02
See application file for complete search history.

(56) References Cited

U.S. PATENT DOCUMENTS 2,280,915 A   4/1942  Johnson
3,171,410 A   3/1965  Towle et al.
(Continued)

FOREIGN PATENT DOCUMENTS

DE   3 935 818   5/1991
DE   4 012 232   10/1991
(Continued)

OTHER PUBLICATIONS

American Heritage® Dictionary of the English Language, Fifth Edition, 2011.*
(Continued)

*Primary Examiner* — Michele M Kidwell
*Assistant Examiner* — Ilya Treyger
(74) *Attorney, Agent, or Firm* — Knobbe Martens Olson & Bear, LLP

(57) ABSTRACT

An apparatus for cleansing wounds with means for stressing the wound bed and optionally tissue surrounding the wound, in which irrigant fluid from a reservoir connected to a conformable wound dressing and wound exudate from the dressing are recirculated by a devise for moving fluid through a flow path which passes through the dressing and a means for fluid cleansing and back to the dressing. The cleansing means (which may be a single-phase, e.g. microfiltration, system or a two-phase, e.g. dialytic system) removes materials deleterious to wound healing, and the cleansed fluid, still containing materials that are beneficial in promoting wound healing, is returned to the wound bed. The means for stressing the wound bed and optionally tissue
(Continued)

surrounding the wound promotes wound healing. The dressing and a method of treatment using the apparatus.

28 Claims, 9 Drawing Sheets

Related U.S. Application Data

11/957,860, filed on Dec. 17, 2007, now Pat. No. 7,753,894, which is a continuation of application No. 10/599,720, filed as application No. PCT/GB2005/001577 on Apr. 26, 2005, now abandoned.

(51) Int. Cl.
    *A61F 13/02*         (2006.01)
    *A61F 13/00*         (2006.01)

(52) U.S. Cl.
    CPC ........... *A61M 35/00* (2013.01); *A61M 1/0058* (2013.01); *A61M 1/0084* (2013.01)

(56) References Cited

U.S. PATENT DOCUMENTS

| | | |
|---|---|---|
| 3,633,567 A | 1/1972 | Sarnoff |
| 3,874,387 A | 4/1975 | Barbieri |
| 3,922,957 A | 12/1975 | Ogle et al. |
| 3,993,080 A | 11/1976 | Loseff |
| 4,112,947 A | 9/1978 | Nehring |
| 4,136,696 A | 1/1979 | Nehring |
| 4,184,510 A | 1/1980 | Murry et al. |
| 4,224,945 A | 9/1980 | Cohen |
| 4,316,466 A | 2/1982 | Babb |
| 4,382,441 A | 5/1983 | Svedman |
| 4,465,485 A | 8/1984 | Kashmer et al. |
| 4,573,965 A | 3/1986 | Russo |
| 4,778,446 A | 10/1988 | Jensen |
| 4,792,328 A | 12/1988 | Beck et al. |
| 4,836,192 A | 6/1989 | Abbate |
| 4,921,488 A | 5/1990 | Maitz et al. |
| 4,936,834 A | 6/1990 | Beck et al. |
| 4,969,880 A | 11/1990 | Zamierowski |
| 5,055,198 A | 10/1991 | Shettigar |
| 5,073,172 A | 12/1991 | Fell |
| 5,100,396 A | 3/1992 | Zamierowski |
| 5,176,663 A | 1/1993 | Svedman et al. |
| 5,261,893 A | 11/1993 | Zamierowski |
| 5,328,614 A | 7/1994 | Matsumura |
| 5,358,494 A | 10/1994 | Svedman |
| 5,380,280 A | 1/1995 | Peterson |
| 5,419,768 A | 5/1995 | Kayser |
| 5,498,338 A | 3/1996 | Kruger et al. |
| 5,549,584 A | 8/1996 | Gross |
| 5,636,643 A | 6/1997 | Argenta et al. |
| 5,645,081 A | 7/1997 | Argenta et al. |
| 5,759,570 A | 6/1998 | Arnold |
| 5,785,508 A | 7/1998 | Bolt |
| 6,102,680 A | 8/2000 | Fraser et al. |
| 6,159,160 A | 12/2000 | Hsei et al. |
| 6,201,164 B1 * | 3/2001 | Wulff ............ A61K 9/0014 602/41 |
| 6,227,825 B1 | 5/2001 | Vay |
| 6,254,567 B1 | 7/2001 | Treu et al. |
| 6,398,767 B1 | 6/2002 | Fleischmann |
| 6,458,109 B1 | 10/2002 | Henley et al. |
| 6,465,708 B1 | 10/2002 | Augustine |
| 6,527,745 B1 | 3/2003 | Kanda et al. |
| 6,626,827 B1 | 9/2003 | Felix et al. |
| 6,676,610 B2 | 1/2004 | Morton et al. |
| 6,685,681 B2 | 2/2004 | Lockwood et al. |
| 6,695,824 B2 | 2/2004 | Howard et al. |
| 6,752,794 B2 | 6/2004 | Lockwood et al. |
| 6,755,807 B2 | 6/2004 | Risk et al. |
| 6,823,905 B1 | 11/2004 | Smith et al. |
| 6,979,324 B2 | 12/2005 | Bybordi et al. |
| 7,004,915 B2 | 2/2006 | Boynton et al. |
| 7,077,832 B2 | 7/2006 | Fleischmann |
| 7,108,683 B2 | 9/2006 | Zamierowski |
| 7,128,719 B2 | 10/2006 | Rosenberg |
| 7,195,624 B2 | 3/2007 | Lockwood |
| 7,214,202 B1 | 5/2007 | Vogel et al. |
| 7,216,651 B2 | 5/2007 | Argenta et al. |
| 7,361,184 B2 | 4/2008 | Joshi |
| 7,447,327 B2 | 11/2008 | Kitamura et al. |
| 7,494,482 B2 | 2/2009 | Orgill et al. |
| 7,524,315 B2 | 4/2009 | Blott et al. |
| 7,534,927 B2 | 5/2009 | Lockwood |
| 7,699,830 B2 | 4/2010 | Martin |
| 7,731,702 B2 | 6/2010 | Bybordi et al. |
| 7,753,894 B2 | 7/2010 | Blott et al. |
| 7,790,945 B1 | 9/2010 | Watson, Jr. |
| 7,794,450 B2 | 9/2010 | Blott et al. |
| 7,828,782 B2 | 11/2010 | Suzuki |
| 7,883,494 B2 | 2/2011 | Martin |
| 7,964,766 B2 | 6/2011 | Blott et al. |
| 8,080,702 B2 | 12/2011 | Blott et al. |
| 8,105,295 B2 | 1/2012 | Blott et al. |
| 8,128,615 B2 | 3/2012 | Blott et al. |
| 8,162,909 B2 | 4/2012 | Blott et al. |
| 8,167,869 B2 | 5/2012 | Wudyka |
| 8,235,955 B2 | 8/2012 | Blott et al. |
| 8,257,327 B2 | 9/2012 | Blott et al. |
| 8,294,586 B2 | 10/2012 | Pidgeon et al. |
| 8,308,714 B2 | 11/2012 | Weston et al. |
| 8,323,264 B2 | 12/2012 | Weston et al. |
| 8,338,402 B2 | 12/2012 | Fry et al. |
| 8,348,910 B2 | 1/2013 | Blott et al. |
| 8,366,692 B2 | 2/2013 | Weston |
| 8,377,016 B2 | 2/2013 | Argenta et al. |
| 8,398,614 B2 | 3/2013 | Blott et al. |
| 8,444,392 B2 | 5/2013 | Turner et al. |
| 8,494,349 B2 | 7/2013 | Gordon |
| 8,529,548 B2 | 9/2013 | Blott et al. |
| 8,535,296 B2 | 9/2013 | Blott et al. |
| 8,617,129 B2 | 12/2013 | Hartwell |
| 8,663,200 B2 | 3/2014 | Weston et al. |
| 9,084,845 B2 | 7/2015 | Adie et al. |
| 2001/0034499 A1 | 10/2001 | Sessions et al. |
| 2002/0161346 A1 | 10/2002 | Lockwood et al. |
| 2003/0021775 A1 | 1/2003 | Freeman |
| 2003/0040687 A1 | 2/2003 | Boynton et al. |
| 2003/0050594 A1 | 3/2003 | Zamierowski |
| 2003/0144619 A1 | 7/2003 | Augustine |
| 2003/0171675 A1 | 9/2003 | Rosenberg |
| 2004/0054338 A1 | 3/2004 | Bybordi et al. |
| 2004/0077977 A1 | 4/2004 | Ella et al. |
| 2004/0127845 A1 | 7/2004 | Renz et al. |
| 2004/0163713 A1 | 8/2004 | Schulze et al. |
| 2005/0130299 A1 | 6/2005 | Suzuki |
| 2005/0155657 A1 | 7/2005 | Kack et al. |
| 2006/0118190 A1 | 6/2006 | Takehana et al. |
| 2006/0191575 A1 | 8/2006 | Naesje |
| 2006/0245947 A1 | 11/2006 | Seto et al. |
| 2007/0021697 A1 | 1/2007 | Ginther et al. |
| 2007/0038172 A1 | 2/2007 | Zamierowski |
| 2007/0129660 A1 | 6/2007 | McLeod et al. |
| 2007/0141125 A1 | 6/2007 | Bourdelais et al. |
| 2007/0219497 A1 | 9/2007 | Johnson et al. |
| 2007/0282283 A1 | 12/2007 | Kaern et al. |
| 2007/0299412 A1 | 12/2007 | Vogel |
| 2008/0094753 A1 | 4/2008 | Brodkin et al. |
| 2008/0208147 A1 | 8/2008 | Argenta et al. |
| 2008/0310980 A1 | 12/2008 | Ramsdorf et al. |
| 2009/0028733 A1 | 1/2009 | Duwel |
| 2009/0054855 A1 | 2/2009 | Blott et al. |
| 2009/0071551 A1 | 3/2009 | Chalich |
| 2009/0105671 A1 | 4/2009 | Daggar et al. |
| 2009/0143753 A1 | 6/2009 | Blott et al. |
| 2009/0221977 A1 | 9/2009 | Blott et al. |
| 2009/0254054 A1 | 10/2009 | Blott et al. |
| 2009/0299255 A1 | 12/2009 | Kazala, Jr. et al. |
| 2009/0299306 A1 | 12/2009 | Buan |
| 2009/0306580 A1 | 12/2009 | Blott et al. |

(56) References Cited

U.S. PATENT DOCUMENTS

| | | |
|---|---|---|
| 2009/0312723 A1 | 12/2009 | Blott et al. |
| 2010/0249733 A9 | 9/2010 | Blott |
| 2011/0000069 A1 | 1/2011 | Ramsdorf et al. |
| 2011/0004171 A1 | 1/2011 | Blott et al. |
| 2011/0009835 A1 | 1/2011 | Blott |
| 2011/0060204 A1 | 3/2011 | Weston |
| 2011/0171044 A1 | 7/2011 | Flanigan |
| 2011/0213320 A1 | 9/2011 | Blott et al. |
| 2012/0001762 A1 | 1/2012 | Turner et al. |
| 2012/0008817 A1 | 1/2012 | Grinker et al. |
| 2012/0301341 A1 | 11/2012 | Ota et al. |
| 2012/0302977 A1 | 11/2012 | Buan et al. |
| 2013/0017110 A1 | 1/2013 | Villagomez et al. |
| 2013/0018338 A1 | 1/2013 | Weston et al. |
| 2013/0118622 A1 | 5/2013 | Patzold et al. |
| 2013/0150813 A1 | 6/2013 | Gordon |
| 2013/0209277 A1 | 8/2013 | Locke et al. |
| 2013/0209279 A1 | 8/2013 | Locke et al. |
| 2013/0209281 A1 | 8/2013 | Locke et al. |
| 2013/0213506 A1 | 8/2013 | Chen et al. |
| 2013/0223979 A1 | 8/2013 | Locke et al. |
| 2013/0280113 A1 | 10/2013 | Miranda et al. |
| 2013/0331823 A1 | 12/2013 | Askem et al. |
| 2013/0340870 A1 | 12/2013 | Ito et al. |
| 2014/0072149 A1 | 3/2014 | Yan et al. |
| 2014/0088528 A1 | 3/2014 | Hartwell |
| 2014/0107599 A1 | 4/2014 | Fink et al. |
| 2015/0025482 A1 | 1/2015 | Begin et al. |

FOREIGN PATENT DOCUMENTS

| | | |
|---|---|---|
| DE | 4 102 684 | 8/1992 |
| DE | 198 44 355 | 4/2000 |
| EP | 0 020 662 | 7/1984 |
| EP | 0 759 521 | 7/1997 |
| EP | 0 777 504 | 10/1998 |
| EP | 0 853 950 | 10/2002 |
| EP | 0 880 953 | 10/2003 |
| EP | 1 449 971 | 8/2004 |
| EP | 1 897 569 | 3/2009 |
| EP | 2 216 573 | 8/2010 |
| EP | 2 830 555 | 2/2015 |
| FR | 1163907 | 10/1958 |
| GB | 114754 | 4/1918 |
| GB | 641061 | 8/1950 |
| GB | 1224009 | 3/1971 |
| GB | 1549756 | 8/1979 |
| GB | 2195255 | 4/1988 |
| GB | 2235877 | 3/1991 |
| GB | 2378392 | 2/2003 |
| SU | 1251912 A1 | 4/1983 |
| WO | WO 84/01904 | 5/1984 |
| WO | WO 90/11795 | 10/1990 |
| WO | WO 91/00718 | 1/1991 |
| WO | WO 92/20299 | 11/1992 |
| WO | WO 00/07653 | 2/2000 |
| WO | WO 00/50143 | 8/2000 |
| WO | WO 02/083046 | 10/2002 |
| WO | WO 02/092783 | 11/2002 |
| WO | WO 02/92783 A2 * | 11/2002 |
| WO | WO 03/074100 | 12/2003 |
| WO | WO 2004/024300 | 3/2004 |
| WO | WO 2004/037334 | 5/2004 |
| WO | WO 2005/046760 | 5/2005 |
| WO | WO 2005/046761 | 5/2005 |
| WO | WO 2005/046762 | 5/2005 |
| WO | WO 2005/051461 | 6/2005 |
| WO | WO 2005/070480 | 8/2005 |
| WO | WO 2005/082435 | 9/2005 |
| WO | WO 2005/105174 | 11/2005 |
| WO | WO 2005/105175 | 11/2005 |
| WO | WO 2005/105176 | 11/2005 |
| WO | WO 2007/019038 | 2/2007 |
| WO | WO 2008/010094 | 1/2008 |
| WO | WO 2012/140180 | 10/2012 |
| WO | WO 2013/006932 | 1/2013 |
| WO | WO 2013/117945 | 8/2013 |
| WO | WO 2013/119854 | 8/2013 |
| WO | WO 2013/133652 | 9/2013 |
| WO | WO 2014/008348 | 1/2014 |

OTHER PUBLICATIONS

Aubrey, D.A., et al., Treatment of the Perineal Wound after Proctectomy by Intermittent Irrigation, Arch. Surg., Oct. 1984, 119, 1141-1144.

Bagautdinov, N. A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).

Chariker, M.E., et al, "Effective Management of Incisional and Cutaneous Fistulae with Closed Suction Wound Drainage," Contemporary Surgery. Jun. 1989, pp. 59-63, vol. 34 USA.

Dilmaghani et al., "A Method for Closed Irrigation and Suction Therapy in Deep Wound Infections," Journal of Bone and Joint Surgery, 1969, vol. 51-A, No. 2, pp. 323-342.

Hartz, R.S., et al., Healing of the Perineal Wound, Arch. Surg., Apr. 1980, 115, 471-474.

NURSING75, Wound Suction: Better Drainage with Fewer Problems, Nursing, vol. 5, No. 10, Oct. 1975, pp. 52-55.

Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).

Svedman, P., "Irrigation Treatment in Split-Thickness Skin Grafting of Intractable Leg Ulcers," Scand J. Plast. Reconst. Surg., 19:211-213, 1985.

Svedman, P., "Irrigation Treatment of Leg Ulcers," The Lancet, Sep. 1983, 532-34.

Svedman, P., A Dressing Allowing Continuous Treatment of a Biosurface, IRCS Med. Science: Biomed. Tech.; Clinic. Med.; Surg. and Transplantation, 1979, 7, p. 221.

Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.

Swift, et al, "Quorum Sensing in *Aeromonas hydrophila* and *Aeromonas salmoncida*: Identification of LuxRI Homologs AhyRI and AsaRI and Their Cognate N-Acylhomoserine Lactone Signal Molecules," J. Bacteriol., 179(17):5271-5281 (1997).

Teder and Svedman et al., "Continuous Wound Irrigation in the Pig," Journal of Investigative Surgery, 1990, vol. 3, pp. 399-407.

Tribble, David E. M.D., An Improved Sump Drain-Irrigation Device of Simple Construction, Archives of Surgery New York, pp. 511-513, 1972 vol. 105.

Urschel, J.D., et al., The Effect of Mechanical Stress on Soft and Hard Tissue Repair; A Review, Br. Journ. Plast. Surg., 1988, 41, 182-186.

Vijanto, J. and J. Raekallio, Local Hyperalimentation of Open Wounds, Br. J. surg., 1976, 63, 427-430.

Westaby, S., et al., "A Wound Irrigation Device", The Lancet, Sep. 2, 1978, pp. 503-504.

Wooding-Scott, Margaret, et al., "No Wound is Too Big for Resourceful Nurses," RN Dec. 1988, pp. 22-25 USA.

Zivadinovic, Gorica, Veljko Dukic, Zivan Maksimovic, Dorde Radak and Predrag Pesko, Vacuum Therapy in the Treatment of Peripheral Blood Vessels, Timocki Medicinski Glasnik (Conference Papers of the 5th Timok Medical Days, Majdanepek, 1986), Year XI, Zajecar, 1986, No. 3-4, pp. 161-164 (with English translation).

EPO Communication Pursuant to Article 94(3) EPC regarding EPO Application No. 05738248.3-1257, Jun. 11, 2008.

International Preliminary Report for International Application No. PCT/GB/2005/001577, Dated Nov. 1, 2006, in 8 pages.

International Preliminary Search Report for International Application No. PCT/GB/2005/001577, Dated Aug. 31, 2005, in 4 pages.

Response to EPO Communication Pursuant to Article 94(3) EPC regarding EPO Application No. 05738248.3-1257, Dec. 9, 2008.

(56) References Cited

OTHER PUBLICATIONS

Written Opinion dated Oct. 27, 2006 in application No. PCT/GB2005/001577 in 7 pages.
U.S. Appl. No. 61/865,516, filed Aug. 13, 2013, Jaecklein et al.
EPO Reply to Examination Report, dated Jun. 11, 2008 for International Application No. PCT/GB2004/004564, date of mailing Dec. 11, 2008 in 7 pages.
European Examination Report for International Application No. PCT/GB2004/004564, date of mailing Jun. 11, 2008 in 3 pages.
International Preliminary Patent Report for International Application No. PCT/GB2004/004564, date of report issuance Dec. 13, 2005 in 8 pages.
International Preliminary Report for International Application No. PCT/GB/2004/004567, Dated Dec. 13, 2005 in 7 pages.
International Preliminary Report for International Application No. PCT/GB/2005/001595 Dated Nov. 1, 2006 in 7 pages.
International Preliminary Report for International Application No. PCT/GB2006/001551, date of mailing Oct. 30, 2007 in 8 pages.
International Preliminary Report for International Application No. PCT/GB2006/001625, date of mailing Oct. 30, 2007 in 8 pages.
International Preliminary Report for International Application No. PCT/GB2006/003416 Date of Report issuance Mar. 18, 2008 in 11 pages.
International Preliminary Report for International Application No. PCT/GB2006/003425, date of mailing Mar. 18, 2008.
International Search Report for International Application No. PCT/GB/2004/004567, Dated Feb. 21, 2005.
International Search Report for International Application No. PCT/GB/2005/001595 Dated Jul. 27, 2005 in 5 pages.
International Search Report for International Application No. PCT/GB2004/004564, date of mailing Feb. 23, 2005 in 4 pages.
International Search Report for International Application No. PCT/GB2004/004566, date of mailing Feb. 23, 2005.
International Search Report for International Application No. PCT/GB2005/001577, mailed on Aug. 31, 2005, in 4 pages.
International Search Report for International Application No. PCT/GB2006/001551, date of mailing Jan. 19, 2007 in 4 pages.
International Search Report for International Application No. PCT/GB2006/001625, date of mailing Jan. 25, 2007 in 3 pages.
International Search Report for International Application No. PCT/GB2006/003416 date of mailing Nov. 30, 2006 in 4 pages.
International Search Report for International Application No. PCT/GB2006/003425, date of mailing Dec. 11, 2006.
International Search Report in related PCT Application No. PCT/GB03/04647, date of Completion Feb. 13, 2004 in 3 pages.
International Search Report in related PCT Application No. PCT/GB03/04647, date of Completion Sep. 9, 2004 in 2 pages.
International Search Report in related PCT Application No. PCT/GB03/04647, date of mailing Feb. 25, 2004.

\* cited by examiner

Section Through X-X

Section Through X-X

WOUND CLEANSING APPARATUS WITH STRESS

CROSS REFERENCE TO RELATED APPLICATIONS

This application is a divisional of U.S. application Ser. No. 12/832,002, filed on Jul. 7, 2010, which is a divisional application of U.S. application Ser. No. 11/957,860, filed on Dec. 17, 2007, now U.S. Pat. No. 7,753,894, which is a continuation application of U.S. application Ser. No. 10/599,720, filed Oct. 6, 2006, which is the U.S. national phase application of PCT/GB2005/001577, filed Apr. 26, 2005, which claims priority to GB0409291.2, filed on Apr. 27, 2004, all of which are hereby incorporated by reference.

BACKGROUND

Field

The present invention relates to apparatus and a medical wound dressing for irrigating, stressing and/or cleansing wounds, and a method of treating wounds using such apparatus for irrigating, stressing and/or cleansing wounds.

It relates in particular to such an apparatus, wound dressing and method that can be easily applied to a wide variety of, but in particular chronic, wounds, to cleanse them of materials that are deleterious to wound healing, whilst retaining materials that are beneficial in some therapeutic aspect, in particular to wound healing.

Background

Before the present invention, aspirating and/or irrigating wounds and apparatus therefor were known, and tended to be used to remove wound exudate during wound therapy. In known forms of such wound therapy, the offtake from the wound, especially when in a highly exuding state, is voided to waste, e.g. to a collection bag.

Materials deleterious to wound healing are removed in this way.

However, materials that are beneficial in promoting wound healing, such as growth factors, naturally occurring anti-inflammatories, and other physiologically active components of the exudate from a wound are lost to the site where they can be potentially of most benefit, i.e. the wound bed, when such therapy is applied.

It thus would be desirable to provide a system of therapy which
  a) can remove materials deleterious to wound healing from wound exudate, whilst retaining materials that are beneficial in promoting wound healing in contact with the wound bed, and/or
  b) which allows fluids containing active amounts of materials that are beneficial in promoting wound healing to pass into and/or through the wound in contact with the wound bed.

Dialysis is a known method of treating bodily fluids such as blood ex vivo, to cleanse them of materials that are deleterious to the body systemically.

Retaining materials that are beneficial in some therapeutic aspect in the treated fluid is not an object of dialysis.

This method of treating bodily fluids is also a systemic therapy, since the treated fluid is returned to within the body.

This is in contrast to a topical therapy in which the treated fluid is recycled outside the body, e.g. to a wound.

Dialysis also requires large amounts either of bodily fluids, such as blood, or of dialysate, and consequently the relevant devices tend not to be portable.

Even when in a highly exuding state, chronic wounds produce relatively little fluid to be treated and relatively little materials that are beneficial in some therapeutic aspect to be retained in the wound and/or its environment.

SUMMARY

It is an object of the present invention
  a) to obviate at least some of the abovementioned disadvantages of known aspiration and/or irrigation therapy systems, and
  b) to provide a system of therapy which
    i) can remove materials deleterious to wound healing from wound exudate, whilst retaining materials that are beneficial in promoting wound healing in contact with the wound bed, and/or
    ii) which allows fluids containing active amounts of materials that are beneficial in promoting wound healing to pass into and/or through the wound in contact with the wound bed.

It is a further object of the present invention
  a) to obviate at least some of the abovementioned disadvantages of known dialysis systems, and
  b) to provide a system of therapy which
    i) can remove materials deleterious to wound healing from wound exudate, whilst retaining materials that are beneficial in promoting wound healing in contact with the wound bed, and
    ii) further allows fluids containing active amounts of materials that are beneficial in promoting wound to pass into and/or through the wound in contact with the wound bed, without affecting the body systemically.

It is a yet further object of the present invention
  a) to obviate at least some of the abovementioned disadvantages of known dialysis systems, and
  b) to provide a system of therapy which
    i) can remove materials deleterious to wound healing from wound exudate, whilst retaining materials that are beneficial in promoting wound healing in contact with the wound bed, and
    ii) further allows fluids containing active amounts of materials that are beneficial in promoting wound to pass into and/or through the wound in contact with the wound bed without affecting the body systemically, and
    iii) is portable.

Additionally, known forms of wound dressing and aspiration and/or irrigation therapy systems often create a wound environment under the backing layer that may result in the loss of optimum performance of the body's own tissue healing processes, and slow healing and/or in weak new tissue growth that does not have a strong three-dimensional structure adhering well to and growing from the wound bed. This is a significant disadvantage, in particular in chronic wounds.

It is an object of the present invention
  a) to obviate at least some of the abovementioned disadvantages of known wound dressing, and
  b) to provide a system of therapy which
    i) can remove materials deleterious to wound healing from wound exudate, whilst retaining materials that are beneficial in promoting wound healing in contact with the wound bed, and
    ii) which creates stress across the wound bed and optionally tissue surrounding the wound, e.g. by applying an optionally varying positive and/or negative pressure to the wound.

Such a stress across the wound bed and optionally tissue surrounding the wound, e.g. an optionally varying positive and/or negative pressure applied to the wound, has been found to result in an increase in improvements to wound healing, such as an increase in cell proliferation, revascularisation, improved breaking strength and reduction of wound recurrence. The resultant tissue growth has a strong three-dimensional structure adhering well to and growing from the wound bed. It also stimulates blood flow in underlying tissue and optionally tissue surrounding the wound.

Removal of fluid by optionally varying negative pressure leads to reduction of interstitial oedema and pressure directly affecting the lymphatic and capillary system, restoring lymph function.

All of these are beneficial to wound healing.

Thus, according to a first aspect of the present invention there is provided an apparatus for irrigating, stressing and/or cleansing wounds, characterised in that it comprises
- a) a fluid flow path, comprising
  - i) a conformable wound dressing, having
    - a backing layer which is capable of forming a relatively fluid-tight seal or closure over a wound and
    - at least one inlet pipe for connection to a fluid supply tube, which passes through and/or under the wound-facing face, and
    - and at least one outlet pipe for connection to a fluid offtake tube, which passes through and/or under the wound-facing face,
    - the point at which the or each inlet pipe and the or each outlet pipe passes through and/or under the wound-facing face forming a relatively fluid-tight seal or closure over the wound,
    - at least one inlet pipe being connected to a fluid recirculation tube, and
    - at least one outlet pipe being connected to a fluid offtake tube: and
  - ii) a means for fluid cleansing having at least one inlet port connected to a fluid offtake tube and at least one outlet port connected to a fluid recirculation tube;
- b) a fluid reservoir connected by a fluid supply tube to an integer of the flow path (optionally or as necessary via means for flow switching between supply and recirculation);
- c) a device for moving fluid through the wound dressing and means for fluid cleansing, and optionally or as necessary the fluid supply tube; and
- d) optionally means for bleeding the flowpath, characterised in that it comprises
- e) means for stressing the wound bed and optionally tissue surrounding the wound; such that fluid may be supplied to fill the flowpath from the fluid reservoir via the fluid supply tube (optionally or as necessary via the means for flow switching) and recirculated by the device through the flow path.

Where any pipe is described in connection with the apparatus as being connected or for connection to a (mating end of a) tube, e.g. a fluid supply tube, fluid recirculation tube or fluid offtake tube, the pipe and the tube may form a single integer in the flow path through which the circulating fluid from the wound passes.

As noted hereinbefore, the present invention in this aspect advantageously provides a means for combining more than one therapy in a single dressing system, such as a) removal of materials deleterious to wound healing from wound exudate, whilst retaining materials that are beneficial in promoting wound healing, and b) promoting wound healing, by stimulating new tissue growth adhering well to and growing from the wound bed, by creating stress across the wound bed and optionally tissue surrounding the wound.

It may aid in the debridement of slough, eschar and necrotic tissue growth from the wound.

In all relevant embodiments of the present apparatus for irrigating, stressing and/or cleansing wounds, it is advantageous that it additionally, where appropriate, comprises a system which can regulate the pressure on the wound bed, under the wound dressing.

Preferably such a system is a conventional automated, programmable system which can maintain the wound at or near an appropriate, desired stress to the wound bed and optionally tissue surrounding the wound, to an appropriate, desired programme while moving fluid over the wound bed and through the means for fluid cleansing at an appropriate, desired rate.

Examples of suitable means for the stimulation of the healing of wounds and tissue adhering well to and growing from the wound bed include applying mechanical stimulus to the wound bed and optionally tissue surrounding the wound via the wound dressing and/or via the fluid under dressing.

Examples of suitable ways in which this can in turn be achieved include applying an optionally varying positive and/or negative pressure at any appropriate point for stressing the wound.

The amplitude of the positive and/or negative pressure on the wound bed and optionally tissue surrounding the wound and/or the fluid thereover may be constant, but more usually is varied, preferably cyclically, either randomly or regularly. Such cyclical variation of the pressure applied to the wound is effectively the application of an amplitude waveform at a desired frequency to apply a desired level of stress to the wound bed and optionally tissue surrounding the wound.

The desired level and regime of stress to the wound bed and optionally tissue surrounding the wound may be applied conventionally by varying the positive and/or negative pressure applied to the wound bed, e.g. by a) varying the rate of the means for moving fluid over the wound bed and through the means for fluid cleansing, as appropriate or desired, e.g. the rate of any pump used to apply positive or negative pressure to the wound bed at any appropriate point for stressing the wound, b) bleeding fluids, especially gases, such as air and nitrogen, but not excluding liquids, such as water and saline, or gas in liquid aerosols; and gels into the flowpath in any appropriate part of the apparatus to vary the pressure applied to the wound to a desired level and/or programme, and/or c) varying the pressure in any inflatable filler within the wound dressing as appropriate or desired, as described in more detail hereinafter.

Preferably, such regular or random variation of the positive and/or negative pressure applied to the wound will be effected by conventional process control devices and/or software.

The stimulation of the healing of wounds in the present invention may also be effected by agitation of the wound bed and/or creating intermittent flow and/or turbulence to stimulate the cells. This can be done preferably by regularly or randomly pulsing a positive and/or negative pressure applied to the wound at any appropriate point for this purpose. Such pulsed variation of the pressure applied to the wound is again effectively the application of an amplitude waveform at a desired frequency to apply a desired level of stress to the wound bed and optionally tissue surrounding the wound.

Pulsing the pressure on the wound may advantageously also provide a means to over-ride pain, similar to TENS.

The range of variation of the pulsed positive and/or negative pressure applied to the wound will be substantially less than the maximum levels of pressure referred to below.

The frequencies of such pulsed stressing across the wound will be substantially higher than those of the cycles of positive and/or negative pressure to the wound bed and optionally tissue surrounding the wound for the stimulation of the healing of wounds referred to above.

The range of variation of the pulsed positive and/or negative pressure applied to the wound will be substantially less than the maximum levels of pressure and than the range of variation in the levels of pressure referred to below.

The frequencies of such pulsed stressing across the wound will usually be substantially higher than those of the cycles of positive and/or negative pressure to the wound bed and optionally tissue surrounding the wound for the stimulation of the healing of wounds referred to above.

Regularly or randomly pulsing any pressure applied to the wound may be effected essentially as described hereinbefore in connection with the variation of the positive and/or negative pressure applied to the wound. Again, such regular or random pulsing of the positive and/or negative pressure applied to the wound may be effected by conventional process control devices and/or software.

Such pulsing of any pressure applied to the wound may be applied as an amplitude modulation of the positive and/or negative pressure applied to the wound bed and optionally tissue surrounding the wound, which in turn may be held constant, but more usually is varied, preferably cyclically, either randomly or regularly.

Where the levels of such pressure above or below, atmospheric are held constant, this is often achieved in the present apparatus, where appropriate, by use of a control device that can regulate the pressure in the wound dressing by bleeding fluids, especially gases, such as air and nitrogen, but not excluding liquids, such as water and saline, or gas in liquid aerosols; and gels into the flowpath in any appropriate part of the apparatus to vary the pressure applied to the wound to a desired level and/or programme.

This often results in any device for moving fluid through the wound that is downstream of the dressing and that applies an overall negative pressure in the wound space, e.g. a vacuum pump, pumping a heterogeneous mixture of liquid wound exudate and irrigant from the wound dressing with bleed gases, such as air and nitrogen. This can result in pulsing of any pressure applied to the wound.

The pumping rate, the rate of bleeding, and the dimensions of the offtake and/or recirculation tubes may be adjusted to maintain the desired balance of pulsing pressure amplitude and frequencies on the wound.

Preferably such a system is a conventional automated, programmable system which can maintain the appropriate pulse regimen to the wound.

Stimulus to the wound bed and optionally tissue surrounding the wound by applying an optionally varying positive and/or negative pressure and agitation of the wound bed to stimulate the cells by regularly or randomly pulsing any pressure applied to the wound are mutually compatible. They may, as appropriate, be applied alone or together.

Thus, an embodiment of the apparatus for irrigating, stressing and/or cleansing wounds of the present invention is characterised in that it comprises means for supplying optionally varying positive and/or negative pressure, which is optionally pulsed, to a wound bed and optionally tissue surrounding the wound for the stimulation of the healing of the wound.

As noted hereinbefore, in the present invention in this aspect, the positive and/or negative pressure on the wound bed and/or the fluid thereover and optionally tissue surrounding the wound may be constant, but more usually is varied, preferably cyclically, either randomly or regularly. Where the pressure on the wound bed and/or the fluid thereover and optionally tissue surrounding is varied, it may be a varying positive or negative pressure, or it may as appropriate vary from positive to negative or vice versa, again preferably cyclically, and either randomly or regularly. It may vary about a constant positive or negative baseline pressure, or less usually about a varying baseline pressure. Examples of maximum levels of such pressure above and below atmospheric include 50% atm. e.g. between 5 and 40% atm., e.g. between 15 and 35% atm.

Examples of suitable frequencies of such regular cycles of pressure for the stimulation of the healing of wounds include 1 to 48 per 24 hr, such as 12 to 24 per 24 hr, e.g. 2 to 1 per hr.

Examples of suitable waveforms of such cycles either regularly or randomly for the stimulation of the healing of wounds include curved, e.g. sinusoidal, random white noise and sawtooth for higher frequencies, and usually square for lower frequencies.

Examples of suitable frequencies of regular pulses for the stimulation of the healing of wounds include 1 to 3000 per min (0.016-50 Hz), e.g. 30 to 60 per min, e.g. 3 to 20 per min, i.e. 0.05 to 0.33 Hz, such as 5 to 10 per min.

Such pulses may be varying positive or negative pressure pulses, or they may as appropriate vary from positive to negative or vice versa, again preferably cyclically, and either randomly or regularly. They may vary about a constant positive or negative baseline pressure or about a varying baseline pressure. Examples of maximum amplitudes for such pulses are up to 10 mm Hg above and below the constant positive or negative baseline pressure, e.g. up to 7 mm Hg or up to 3 mm Hg.

Examples of suitable waveforms of such pulses either regularly or randomly for the stimulation of the healing of wounds include curved, e.g. sinusoidal, random white noise sawtooth, square and a systolic-diastolic asymmetric sawtooth.

Where the amplitude of regular cycles of pressure is modulated by superimposed regular pulses for the stimulation of the healing of wounds, examples of suitable frequencies of the combination include those where the carrier frequency is 1 to 48 per 24 hours and the superimposed frequency of the pressure pulses is 1 to 0.05 Hz, both with the respective amplitudes noted above.

Examples of suitable waveforms of the cycles and the superimposed pulses may be regular or random and include curved, e.g. sinusoidal, random white noise sawtooth, square and a systolic-diastolic asymmetric sawtooth.

Examples of means for applying an optionally varying positive and/or negative pressure at any appropriate point for stressing the wound and/or regularly or randomly pulsing any pressure applied to the wound for promoting wound healing, whether applied alone or together, include a wound dressing as hereinbefore defined that comprises one or more expandable and contractible modules capable of applying pressure to the wound bed and optionally tissue surrounding the wound at any appropriate point for stressing the wound.

Examples of other suitable means of applying mechanical stimulus to the wound by optionally varying positive and/or negative pressure include a magnetic fluid in a chamber or other hollow structure under the backing layer of the dressing in contact with the wound bed and/or the fluid thereover to which a regularly or randomly (preferably cyclically) varying and/or pulsing external magnetic field is applied. However, such means are less favoured.

Thus, one favoured embodiment of the apparatus for irrigating, stressing and/or cleansing wounds is characterised in that it comprises a wound dressing as hereinbefore defined that comprises one or more expandable and contractible modules.

These are capable of applying pressure to the wound bed and optionally tissue surrounding the wound at any appropriate point for stressing the wound.

This means should be capable of maintaining the pressure on the wound bed and/or the fluid thereover and optionally tissue surrounding the wound at a constant level, but more usually it should also be capable of regularly or randomly (preferably cyclically) varying and/or pulsing the pressure applied to the wound, all at or near an appropriate, desired level of stress to the wound bed and optionally tissue surrounding the wound, to an appropriate, desired programme while moving fluid over the wound bed and through the means for fluid cleansing at an appropriate, desired rate.

Examples of suitable modules capable of applying pressure to the wound bed at any appropriate point for stressing the wound include a module in the wound dressing may be made of a polymer that can be electrically stimulated to change shape repeatedly as appropriate frequencies.

A preferred module is a fluid-inflatable body that lies in the wound in use.

Thus, one favoured embodiment of the apparatus for irrigating, stressing and/or cleansing wounds is characterised in that it comprises a wound dressing as hereinbefore defined that comprises one or more fluid-inflatable modules capable of applying pressure to the wound bed at any appropriate point for stressing the wound.

This is capable of maintaining the pressure on the wound bed and/or the fluid thereover at a constant level, but more usually it is also capable of regularly or randomly (preferably cyclically) varying and/or pulsing the pressure applied to the wound, all at or near an appropriate, desired level of stress to the wound bed, to an appropriate, desired programme while moving fluid over the wound bed.

The module or modules is/are (usually cyclically) inflated and deflated by admitting and releasing fluid.

Once the inflatable body has been inflated, it may be deflated as appropriate or desired, and then reinflated to again apply a positive pressure to the wound, and the cycle may be repeated as appropriate or desired.

Alternatively, it may be partially filled with an elastically resilient material, such as an elastomeric foam, that in its rest state is capable of applying a working pressure to the wound bed. The body may then be deflated as appropriate or desired, and then reinflated under the action of its filler material to again apply a positive pressure to the wound, and the cycle may be repeated as appropriate or desired.

Examples of forms of the body that are suitable such expandable and contractible modules capable of applying pressure to the wound bed at any appropriate point for stressing the wound include fluid-inflatable fillers and fluid-inflatable irrigant inlet manifolds comprised in the dressing as described hereinafter in greater detail.

Where the module is a fluid-inflatable filler, examples of suitable fluids include gases, such as air and nitrogen; liquids, such as water and saline; gas in liquid aerosols; and gels such as those described in greater detail hereinafter. Preferred fluids include gases, such as air or nitrogen.

Where the module is a fluid-inflatable irrigant inlet manifold comprised in the dressing as described hereinafter in greater detail, it will be stimulated to change shape as appropriate and optionally at desired frequencies by inflation with irrigant, followed as desired by deflation.

Examples of both are included hereinafter.

Examples of such fillers include a substantially flat film, sheet or membrane, defining a chamber, pouch or other structure of the backing layer, e.g. of polymer film, which can contain the fluid.

It is provided with an inflation device for moving inflation fluid to the filler, and is connected to it by an inflation tube which communicates with its internal space.

The inflation device may also serve as a deflation device for moving inflation fluid from the filler, and the inflation tube also serves as a deflation tube.

Alternatively or additionally, where appropriate the filler as hereinbefore defined may have a deflation pipe and a bleed valve to waste, e.g. to a collection bag if a non-gaseous fluid is used.

The inflation device for moving then only serves as an inflation device to apply a positive pressure on the wound bed.

Less usually, the filler may have an inflation pump and a deflation pump.

Where it lies under the backing layer of the wound dressing of the apparatus of the invention, the inflation tube may run to the filler within the wound under the wound-facing face of the wound dressing.

However, the inflation tube may be connected to an inflation pipe that passes through the wound-facing face of the backing layer, the point at which the inflation pipe passes through the wound-facing face forming a relatively fluid-tight seal.

The inflation pipe may be in the form of an aperture, such as a funnel hole, opening, orifice, luer, slot or port for connection as a female member respectively to a mating end of the inflation tube (optionally or as necessary via means for forming a tube, pipe or hose, or nozzle).

Where the pipe passes through, rather than under the backing layer, the backing layer may often have a rigid and/or resiliently inflexible or stiff area to resist any substantial play between the or each pipe and the or each mating tube, or deformation under pressure in any direction.

It may often be stiffened, reinforced or otherwise strengthened by a boss projecting distally (outwardly from the wound) around each relevant tube, pipe or hose, or nozzle, hole, opening, orifice, luer, slot or port for connection to a mating end of the inflation tube.

The components may be a push, snap or twist-lock fit with each other.

The minimum calibre of the inflation tube and pipe must be sufficient for them to permit as rapid inflation and deflation of the filler as is desired.

Suitably the range of cross-dimensions of the bore may be 0.5 to 6 mm, e.g. 1.5 to 2 mm.

Each should be resiliently flexible, and preferably soft with good conformability. This can be done for example by forming it of a suitable material, e.g. a resilient thermoplastic.

Examples of suitable inflation device for moving fluid into the filler include pumps. As noted above, the inflation device may also serve as a deflation device for moving inflation fluid from the filler, and the inflation tube also serves as a deflation tube. In such case, the pump must be a reversible pump used to increase and decrease the pressure on the wound bed as desired.

Subject to this consideration, the type and/or capacity of the device will also be largely determined by the appropriate or desired positive or negative pressure to the wound bed, the nature of the fluid, i.e. whether it is a gas, such as air and nitrogen; a liquid, such as water and saline; a gas in liquid aerosol; or a gel;

the desired frequencies and waveforms of such cycles either regularly or randomly.

The following types of pump may be used to apply positive pressure, as desired to the filler through an inflation tube which communicates with its internal space:

reciprocating pumps, such as:
syringe or piston pumps—providing high pressure and high accuracy;
diaphragm pumps—where pulsations of one or two flexible diaphragms displace liquid while check valves control the direction of the fluid flow e.g. preferably a small portable diaphragm pump.
and
rotary pumps, such as:
centrifugal pumps—with rotating vaned disk attached to a drive shaft moving fluid without pulsation as it spins. The outlet can be restricted without damaging the pump.
peristaltic pumps—with rollers on a rotor acting on fluid in a tube, e.g. preferably a small portable peristaltic pump.

Of these, only piston pumps and rotary pumps, such as centrifugal pumps and peristaltic pumps are readily reversible pumps that may be used to increase and decrease the pressure on the wound bed as desired.

Subject to this consideration, preferred reversible pumps include a small portable peristaltic pump.

Preferred non-reversible pumps to be used with a bleed valve to the filler then include a small portable syringe pump (which is often used once and then disposed of) or small portable diaphragm pump, e.g. a sphygmometric pump.

As noted hereinbefore, stimulation of the healing of wounds in the present invention may also be effected by regularly or randomly pulsing a pressure applied to the wound at any appropriate point for this purpose.

Such pulsed pressure on the wound may be provided by some types of the device for moving fluid into the filler.

Where the module is a fluid-inflatable irrigant inlet manifold comprised in the dressing as described herein after in greater detail, it will be stimulated to change shape as appropriate and optionally at desired frequencies by inflation with irrigant, followed as desired by partial deflation.

The device for moving fluid through the wound and means for fluid cleansing is used to move irrigant to inflate the inlet manifold and apply a positive pressure to the wound bed. As noted hereinafter, the device may suitably be a pump.

As noted hereinbefore, the pressure on the wound bed may be constant, but may be varied, preferably cyclically, either randomly or regularly.

To achieve this, the present apparatus, where appropriate, comprises a system that can regulate the pump output to the inlet manifold in the wound dressing.

Preferably such a system is a conventional automated, programmable system which can maintain the wound at or near an appropriate, desired flow stress to the wound bed to an appropriate, desired programme while moving fluid over the wound bed.

As noted hereinbefore, stimulation of the healing of wounds in the present invention may also be effected by regularly or randomly pulsing a pressure applied to the wound at any appropriate point for this purpose.

Such pulsed flow across the wound may be provided by some types of the device for moving fluid through the wound and means for fluid cleansing.

Certain diaphragm pumps described hereinafter in greater detail will be appropriate for this purpose, as are certain peristaltic pumps, and an electromechanical oscillator directly coupled to the wound dressing, will be suitable.

Suitable materials for such modules of any type include synthetic polymeric materials that do not absorb aqueous fluids, such as polyolefins, polysiloxanes and polyesters. They may be hydrophilic, and thus also include hydrophilic polyurethanes. They also include thermoplastic elastomers and elastomer blends, for example copolymers, such as ethyl vinyl acetate polystyrene and elastomeric polyurethane formed by solution casting.

In all embodiments of the apparatus of this first aspect of the present invention for aspirating, irrigating and/or cleansing wounds, a particular advantage is the tendency of the wound dressing to conform to the shape of the bodily part to which it is applied.

The wound dressing comprises a backing layer with a wound-facing face which is capable of forming a relatively fluid-tight seal or closure over a wound and at least one inlet pipe for connection to a fluid supply tube or recirculation tube, which passes through and/or under the wound-facing face, and at least one outlet pipe for connection to a fluid offtake tube, which passes through and/or under the wound-facing face, the point at which the or each inlet pipe and the or each outlet pipe passes through and/or under the wound-facing face forming a relatively fluid-tight seal or closure.

The term 'relatively fluid-tight seal or closure' is used herein to indicate one which is fluid- and microbe-impermeable and permits a positive or negative pressure of up to 50% atm., more usually up to 15% atm. to be applied to the wound. The term 'fluid' is used herein to include gels, e.g. thick exudate, liquids, e.g. water, and gases, such as air, nitrogen, etc.

The shape of the backing layer that is applied may be any that is appropriate to aspirating, irrigating and/or cleansing the wound across the area of the wound.

Examples of such include a substantially flat film, sheet or membrane, or a bag, chamber, pouch or other structure of the backing layer, e.g. of polymer film, which can contain the fluid.

The backing layer may be a film, sheet or membrane, often with a (generally uniform) thickness of up to 100 micron, preferably up to 50 micron, more preferably up to 25 micron, and of 10 micron minimum thickness.

Its largest cross-dimension may be up to 500 mm (for example for large torso wounds), up to 100 mm (for example for axillary and inguinal wounds), and up to 200 mm for limb wounds (for example for chronic wounds, such as venous leg ulcers and diabetic foot ulcers.

Desirably the dressing is resiliently deformable, since this may result in increased patient comfort, and lessen the risk of inflammation of a wound.

Suitable materials for it include synthetic polymeric materials that do not absorb aqueous fluids, such as polyolefins, such as polyethylene e.g. high-density polyethylene, polypropylene, copolymers thereof, for example with vinyl acetate and polyvinyl alcohol, and mixtures thereof; polysiloxanes;

polyesters, such as polycarbonates; polyamides, e.g. 6-6 and 6-10, and hydrophobic polyurethanes.

They may be hydrophilic, and thus also include hydrophilic polyurethanes.

They also include thermoplastic elastomers and elastomer blends, for example copolymers, such as ethyl vinyl acetate, optionally or as necessary blended with high-impact polystyrene.

They further include elastomeric polyurethane, particularly polyurethane formed by solution casting.

Preferred materials for the present wound dressing include thermoplastic elastomers and curable systems.

The backing layer is capable of forming a relatively fluid-tight seal or closure over the wound and/or around the inlet and outlet pipe(s).

However, in particular around the periphery of the wound dressing, outside the relatively fluid-tight seal, it is preferably of a material that has a high moisture vapour permeability, to prevent maceration of the skin around the wound.

It may also be a switchable material that has a higher moisture vapour permeability when in contact with liquids, e.g. water, blood or wound exudate. This may, e.g. be a material that is used in Smith & Nephew's Allevyn™, IV3000™ and OpSite™ dressings.

The periphery of the wound-facing face of the backing layer may bear an adhesive film, for example, to attach it to the skin around the wound. This may, e.g. be a pressure-sensitive adhesive, if that is sufficient to hold the wound dressing in place in a fluid-tight seal around the periphery of the wound-facing face of the wound dressing.

Alternatively or additionally, where appropriate a light switchable adhesive could be used to secure the dressing in place to prevent leakage.

(A light switchable adhesive is one the adhesion of which is reduced by photocuring. Its use can be beneficial in reducing the trauma of removal of the dressing.)

Thus, the backing layer may have a flange or lip extending around the proximal face of the backing layer, of a transparent or translucent material (for which it will be understood that materials that are listed above are amongst those that are suitable).

This bears a film of a light switchable adhesive to secure the dressing in place to prevent leakage on its proximal face, and a layer of opaque material on its distal face.

To remove the dressing and not cause excessive trauma in removal of the dressing, the layer of opaque material on the distal face of the flange or lip extending around the proximal wound is removed prior to application of radiation of an appropriate wavelength to the flange or lip.

The periphery of the wound dressing, outside the relatively fluid-tight seal, that bears an adhesive film to attach it to the skin around the wound, may be of a material that has a high moisture vapour permeability or is a switchable material.

In such case, the adhesive film, if continuous, should also have a high or switchable moisture vapour permeability, e.g. be an adhesive such as used in Smith & Nephew's Allevyn™, IV3000™ and OpSite™ dressings.

Where a vacuum, is applied to hold the wound dressing in place in a fluid-tight seal around the periphery of the wound-facing face of the wound dressing, the wound dressing may be provided with a silicone flange or lip to seal the dressing around the wound. This removes the need for adhesives and associated trauma to the patient's skin.

Where the interior of, and the flow of irrigant and/or wound exudate to and through, the dressing is under any significant positive pressure, which will tend to act at peripheral points to lift and remove the dressing off the skin around the wound.

In such use of the apparatus, it may thus be necessary to provide means for forming and maintaining such a seal or closure over the wound against such positive pressure on the wound, to act at peripheral points for this purpose.

Examples of such means include light switchable adhesives, as above, to secure the dressing in place to prevent leakage.

Since the adhesion of a light switchable adhesive is reduced by photocuring, thereby reducing the trauma of removal of the dressing, a film of a more aggressive adhesive may be used, e.g. on a flange, as above.

Examples of suitable fluid adhesives for use in more extreme conditions where trauma to the patient's skin is tolerable include ones that consist essentially of cyanoacrylate and like tissue adhesives, applied around the edges of the wound and/or the proximal face of the backing layer of the wound dressing, e.g. on a flange or lip.

Further suitable examples of such means include adhesive (e.g. with pressure-sensitive adhesive) and non-adhesive, and elastic and non-elastic straps, bands, loops, strips, ties, bandages, e.g. compression bandages, sheets, covers, sleeves, jackets, sheaths, wraps, stockings and hose, e.g. elastic tubular hose or elastic tubular stockings that are a compressive fit over a limb wound to apply suitable pressure to it when the therapy is applied in this way; and inflatable cuffs, sleeves, jackets, trousers, sheaths, wraps, stockings and hose that are a compressive fit over a limb wound to apply suitable pressure to it when the therapy is applied in this way.

Such means may each be laid out over the wound dressing to extend beyond the periphery of the backing layer of the wound dressing, and as appropriate will be adhered or otherwise secured to the skin around the wound and/or itself and as appropriate will apply compression (e.g. with elastic bandages, stockings) to a degree that is sufficient to hold the wound dressing in place in a fluid-tight seal around the periphery of the wound.

Such means may each be integral with the other components of the dressing, in particular the backing layer.

Alternatively, it may be permanently attached or releasably attached to the dressing, in particular the backing layer, with an adhesive film, for example, or these components may be a Velcro™, push snap or twist-lock fit with each other.

The means and the dressing may be separate structures, permanently unattached to each other.

In a more suitable layout for higher positive pressures on the wound, a stiff flange or lip extends around the periphery of the proximal face of the backing layer of the wound dressing as hereinbefore defined.

The flange or lip is concave on its proximal face to define a peripheral channel or conduit. It has a suction outlet that passes through the flange or lip to communicate with the channel or conduit and may be connected to a device for applying a vacuum, such as a pump or a piped supply of vacuum.

The backing layer may be integral with or attached, for example by heat-sealing, to the flange or lip extending around its proximal face.

To form the relatively fluid-tight seal or closure over a wound that is needed and to prevent passage of irrigant and/or exudate under the periphery of the wound-facing face of the wound dressing, in use of the apparatus, the dressing is set on the skin around the wound.

The device then applies a vacuum to the interior of the flange or lip, thus forming and maintaining a seal or closure acting at peripheral points around the wound against the positive pressure on the wound.

With all the foregoing means of attachment, and means for forming and maintaining a seal or closure over the wound, against positive or negative pressure on the wound at peripheral points around the wound, the wound dressing sealing periphery is preferably of a generally round shape, such as an ellipse, and in particular circular.

To form the relatively fluid-tight seal or closure over a wound and around the inlet pipe(s) and outlet pipe(s) at the point at which they pass through and/or under the wound-facing face, the backing layer may be integral with these other components.

The components may alternatively just be a push, snap or twist-lock fit with each other, or adhered or heat-sealed together.

The or each inlet pipe or outlet pipe may be in the form of an aperture, such as a funnel, hole, opening, orifice, luer, slot or port for connection as a female member respectively to a mating end of a fluid recirculation tube and/or fluid supply tube (optionally or as necessary via means for forming a tube, pipe or hose, or nozzle); or a fluid offtake tube.

Where the components are integral they will usually be made of the same material (for which it will be understood that materials that are listed above are amongst those that are suitable).

Where, alternatively, they are a push, snap or twist-lock fit, the may be of the same material or of different materials. In either case, materials that are listed above are amongst those that are suitable for all the components.

The or each pipe will generally pass through, rather than under the backing layer.

In such case, the backing layer may often have a rigid and/or resiliently inflexible or stiff area to resist any substantial play between the or each pipe and the or each mating tube, or deformation under pressure in any direction.

It may often be stiffened, reinforced or otherwise strengthened by a boss projecting distally (outwardly from the wound) around each relevant tube, pipe or hose, or nozzle, hole, opening, orifice, luer, slot or port for connection to a mating end of a fluid recirculation tube and/or fluid supply tube or fluid offtake tube.

Alternatively or additionally, where appropriate the backing layer may have a stiff flange or lip extending around the proximal face of the backing layer to stiffen, reinforce or otherwise strengthen the backing layer.

The wound dressing may not comprise any integer under the backing layer in the wound in use, other than the ribs or ridges mentioned herein.

To be suitable for use, in particular to impose pressure on the wound bed,
  a) the interior of the wound dressing should conform to the wound bed, even for a wound in a highly exuding state, and
  b) the wound facing face of the dressing, e.g. a fluid-inflatable module as described hereinbefore, should contact or lie very close to the wound bed.

In particular with relatively high concentrations of materials that are deleterious to wound healing, it may be advantageous to provide a system where wound irrigant and/or wound exudate may be distributed more evenly, or pass in a more linear path under the dressing over the wound bed.

Accordingly, one form of the dressing is provided with a wound filler under the backing layer.

This is favourably a resiliently flexible, e.g. elastomeric, and preferably soft, structure with good conformability to wound shape.

It is urged by its own resilience against the backing layer to apply gentle pressure on the wound bed.

The wound filler may be integral with the other components of the dressing, in particular the backing layer.

Alternatively, it may be permanently attached to them/it, with an adhesive film, for example, or by heat-sealing, e.g. to a flange or lip extending from the proximal face, so as not to disrupt the relatively fluid-tight seal or closure over the wound that is needed.

Less usually, the wound filler is releasably attached to the backing layer, with an adhesive film, for example, or these components may be a push, snap or twist-lock fit with each other.

The wound filler and the backing layer may be separate structures, permanently unattached to each other.

If there is a fluid-inflatable module that lies in the wound in use, such as a fluid-inflatable irrigant inlet manifold comprised in the dressing as described hereinafter in greater detail, then the wound filler may be or comprise a solid integer, favourably a resiliently flexible, e.g. elastomeric, and preferably soft, structure with good conformability to wound shape.

Examples of suitable forms of such wound fillers are foams formed of a suitable material, e.g. a resilient thermoplastic.

Preferred materials for the present wound dressing include reticulated filtration polyurethane foams with small apertures or pores.

It may also be in the form of, or comprise one or more conformable non-inflatable hollow bodies defined by a film, sheet or membrane, such as a bag, chamber, pouch or other structure, filled with a fluid or solid that urges it to the wound shape.

Examples of suitable fluids for filling such non-inflatable hollow body or bodies defined by a film, sheet or membrane include gases, such as air, nitrogen and argon, more usually air, at a small positive pressure above atmospheric; and liquids, such as water, saline.

Examples also include gels, such as silicone gels, e.g. CaviCare™ gel, or preferably cellulosic gels, for example hydrophilic cross-linked cellulosic gels, such as Intrasite™ cross-linked materials. Examples also include aerosol foams, where the gaseous phase of the aerosol system is air or an inert gas, such as nitrogen or argon, more usually air, at a small positive pressure above atmospheric; and solid particulates, such as plastics crumbs or beads.

If there is no fluid-inflatable, module the filler should be or comprise a fluid-inflatable module. It may be in the form of, or comprise one or more conformable hollow bodies defined by a film, sheet or membrane, such as a bag, chamber, pouch or other structure, filled with a fluid or solid that urges it to the wound shape.

It will be stimulated to change shape as appropriate and optionally at desired frequencies by inflation with fluid, followed as desired by deflation, as described hereinbefore.

This is capable of maintaining the pressure on the wound bed and optionally tissue surrounding the wound and/or the fluid thereover at a constant level.

More usually, however, it is also capable of regularly or randomly (preferably cyclically) varying and/or pulsing the pressure applied to the wound, all at or near an appropriate, desired level of stress to the wound bed and optionally tissue surrounding the wound, to an appropriate, desired programme while moving fluid over the wound bed The film, sheet or membrane of such a filler often has a (generally uniform) thickness similar to that of films or sheets used in conventional wound dressing backing layers.

That is, up to 100 micron, preferably up to 50 micron, more preferably up to 25 micron, and of 10 micron minimum thickness, and is often resiliently flexible, e.g. elastomeric, and preferably soft.

Such a filler is often integral with the other components of the dressing, in particular the backing layer, or permanently attached to them/it, with an adhesive film, for example, or by heat-sealing, e.g. to a flange.

Examples of suitable fluids for inflating the hollow body or bodies defined by a film, sheet or membrane include gases, such as air, nitrogen and argon, more usually air, at a small positive pressure above atmospheric; and liquids, such as water, saline.

Examples also include gels, such as silicone gels, e.g. CaviCare™ gel, or preferably cellulosic gels, for example hydrophilic cross-linked cellulosic gels, such as Intrasite™ cross-linked materials. Examples also include aerosol foams, where the gaseous phase of the aerosol system is air or an inert gas, such as nitrogen or argon, more usually air, at a small positive pressure above atmospheric.

Of course, if the backing layer is a sufficiently conformable and/or e.g. an upwardly dished sheet, the backing layer may lie under the wound filler, rather than vice versa.

In this type of layout, in order for the wound filler to urge the wound dressing towards the wound bed, it will usually have to be firmly adhered or otherwise releasably attached to the skin around the wound.

This is especially the case in those embodiments where the wound filler and the backing layer are separate structures, permanently unattached to each other.

In such a layout for deeper wounds when the therapy is applied in this way, the means for such attachment may also form and maintain a seal or closure over the wound.

Where the filler is over the backing layer, and the fluid inlet pipe(s) and outlet pipe(s) pass through the wound-facing face of the backing layer, they may run through or around the wound filler over the backing layer.

One form of the dressing is provided with a wound filler under the backing layer that is or comprises a fluid-inflatable irrigant inlet manifold, as described hereinafter in greater detail. It will be stimulated to change shape as appropriate and optionally at desired frequencies by inflation with irrigant, followed as desired by deflation.

This may be a resiliently flexible, e.g. elastomeric, and preferably soft, hollow body defined by a film, sheet or membrane, such as a bag, chamber, pouch or other structure, with apertures, holes, openings, orifices, slits or slots, or tubes, pipes, tubules or nozzles. It communicates with at least one inlet or outlet pipe through at least one aperture, hole, opening, orifice, slit or slot.

The fluid contained in the hollow body will then be the circulating fluid in the apparatus.

The type of the fluid-inflatable module(s) that is/are used as a component of a wound dressing may be largely determined by the depth and/or capacity of the wound.

Thus, for shallower wounds, examples of suitable such modules as a component of a wound dressing include ones that consist essentially of a) a shallow fluid-inflatable filler, or b) one or more fluid-inflatable inlet manifolds that deliver the circulating fluid directly to the wound bed, optionally with one or more outlet manifolds that collect the fluid directly from the wound.

A more suitable wound filler for deeper wounds is one which comprises a) a shallow fluid-inflatable filler, or b) one or more fluid-inflatable inlet manifolds that deliver the circulating fluid directly to the wound bed, that at least partly surround(s) a solid integer, optionally with one or more outlet manifolds that collect the fluid directly from the wound. This may provide a system with better rigidity for convenient handling.

Where a fluid-inflatable module is or comprises a fluid-inflatable inlet manifold, it is provided with apertures admitting fluids to the wound bed under the wound dressing. These may inter alia be in the form of microapertures in a semi-permeable membrane.

Such an inlet manifold may be used with an outlet manifold. Suitable layouts of integers under the dressing include ones where either or both manifolds are regular, e.g. elliptical or circular, or irregular annular or toroidal.

The inlet and/or outlet tubes, the fluid recirculation tube and the fluid supply tube, etc. may be of conventional type, e.g. of elliptical or circular cross-section, and may suitably have a uniform cylindrical bore, channel, conduit or passage throughout their length.

Depending on the desired fluid volume flow rate of irrigant and/or wound exudate from the wound, and the desired amount in recirculation, suitably the largest cross-dimension of the bore may be up to 10 mm for large torso wounds, and up to 2 mm for limb wounds.

The tube walls should suitably thick enough to withstand any positive or negative pressure on them, in particular if the volume of irrigant and/or wound exudate from the wound in recirculation is increased by continuing addition to it of wound exudate, and/or fluid passing from a cleansing fluid through a selectively permeable integer, for example the polymer film, sheet or membrane of a two-phase system, such as an dialysis unit. However, as noted below with regard to pumps, the prime purpose of such tubes is to convey fluid irrigant and exudate through the length of the apparatus flow path, rather than to act as pressure vessels. The tube walls may suitably be at least 25 micron thick.

The bore or any perforations, apertures, holes, openings, orifices, slits or slots along the pipes, etc. or in the hollow body or each of the hollow bodies may be of small cross-dimension.

They may then effectively form a macroscopic and/or microscopic filter for particulates including cell debris and micro-organisms, whilst allowing proteins and nutrients to pass through.

Such tubes, pipes or hoses, etc. through and/or around the filler, whether the latter is a solid integer and/or one or more resiliently flexible or conformable hollow bodies, are described in further detail hereinbefore in connection with the inlet pipe(s) and outlet pipe(s).

Returning to the flowpath of the apparatus, the means for flow switching between supply and recirculation may take any form that enables the wound simultaneously to be a) put into communication with the fluid reservoir but b) closed to the fluid recirculation tube, and c) vice versa.

Thus, if there is only one inlet pipe that passes through and/or under the wound-facing face of the wound dressing, the fluid reservoir is connected by the fluid supply tube to the flow path via means for flow switching as desired the into a fluid recirculation tube or a fluid offtake tube.

In this case, the means for flow switching between supply and recirculation may be a regulator, such as a T-valve. This is connected in turn to two parts of a fluid recirculation tube or a fluid offtake tube and the fluid supply tube, such that the desired flow switching between supply and recirculation is achieved.

If there are two or more inlet pipes, these may be connected respectively to a fluid supply tube or fluid recirculation tube, respectively having a first regulator and a second regulator, such as a valve or other control device for admitting fluids into the wound.

The desired flow switching between supply and recirculation is achieved by respectively having the first regulator open when the second regulator is shut, and vice versa.

The means for bleeding the flowpath may be situated in any appropriate part of the apparatus that is in contact with the irrigant and/or wound exudate, but is usually within the offtake and/or recirculation tubes. However, it is often as far downstream of and away from the reservoir and the fluid supply tube as possible, so that it may be used to prime the whole of the flowpath from the fluid reservoir via the fluid supply tube.

It may be a regulator, such as a valve or other control device, e.g. a T-valve that is turned to switch between bleed and recirculation, for bleeding fluids from the apparatus, e.g. to a waste reservoir, such as a collection bag.

Alternatively, flow switching between supply and recirculation may not be desired, but rather concomitant bleeding and/or recirculation is desired. The latter may occur when the volume of irrigant and/or wound exudate in recirculation is increased by continuing addition to it of
  a) wound exudate, and/or
  b) fluid passing from a cleansing fluid through a selectively permeable integer, for example in a system such as a dialysis unit.

The means for bleeding the offtake and/or recirculation tubes may then be provided in the form of a regulator, such as a simple valve or other control device for admitting or blocking the passage of irrigant and/or exudate through a bleed line branching from the recirculation path.

The means for fluid cleansing may as desired be a 'single-phase system'.

In this, the circulating fluid from the wound and the fluid reservoir passes through a self-contained system in which materials deleterious to wound healing are removed and the cleansed fluid, still containing materials that are beneficial in promoting wound healing, is returned via the recirculation tube to the wound bed. Such systems are described in further detail hereinafter in connection with the means for fluid cleansing.

Alternatively, where appropriate it may be provided in the form of a two-phase system, such as a dialysis unit, or a biphasic liquid extraction unit.

In this, the circulating fluid from the wound and the fluid reservoir passes through a system in which the fluid recirculates in indirect or (less usually, direct) contact with a second fluid (dialysate) phase, more usually a liquid, in which materials deleterious to wound healing are removed and the cleansed fluid, still containing materials that are beneficial in promoting wound healing, is returned via the recirculation tube to the wound bed. Such systems are described in further detail hereinafter in connection with the means for fluid cleansing.

In use, typically, the means for flow switching between supply and recirculation tubes is set to admit fluid into the wound from the fluid reservoir but to close the wound to the fluid recirculation tube.

Then, any means for bleeding the offtake and/or recirculation tubes are is opened and the device for moving fluid through the wound and means for fluid cleansing is started.

The capacity of the apparatus flow path and the flow rate of irrigant and/or wound exudate from the wound will largely determine whether it is appropriate to run the device to prime the apparatus throughout the whole length of the apparatus flow path, i.e. to displace any existing fluid reservoir (often air) from the fluid recirculation path, and for how long it should be run. Typically, there is a preponderance of irrigant from the fluid reservoir over wound exudate in recirculation, so that use of the device for moving fluid through the wound is appropriate for this purpose.

It is allowed to run until the apparatus is primed throughout the whole length of the apparatus flow path.

Then, typically the means for bleeding the offtake and/or recirculation tubes is closed, and the means for flow switching between supply and recirculation tubes is set to close the wound to the fluid reservoir but to admit fluid into the wound from the fluid recirculation tube.

If the means for fluid cleansing is a two-phase system, such as a dialysis unit, or a biphasic extraction unit, the cleansing fluid is typically set in motion in contact with the surface of the selectively permeable integer, for example the polymer film, sheet or membrane. Of course, the cleansing fluid may less usually be static, and then this step is omitted.

As noted below in more detail, the volume of irrigant and/or wound exudate from the wound in recirculation may be increased by continuing addition to it of
  a) wound exudate, and/or
  b) fluid passing from a cleansing fluid through a selectively permeable integer, for example the polymer film, sheet or membrane of a two-phase system, such as an dialysis unit.

Additionally or alternatively, it may be desired to apply a negative pressure to the wound by means of a device for moving fluid through the wound and means for fluid cleansing applied to the fluid in recirculation in the fluid recirculation tube downstream of and away from the wound dressing.

In such case, it may be desirable to provide a system in which concomitant bleeding and/or recirculation is possible, and to make the necessary adjustments to maintain the desired balance of fluid in recirculation by means of the means for bleeding the offtake and/or recirculation tubes.

The volume of irrigant and/or wound exudate from the wound in recirculation may be decreased by continuing loss from it of fluid passing from a cleansing fluid through a selectively permeable integer, for example in a system such as a dialysis unit.

Additionally or alternatively, it may be desired to apply a positive pressure to the wound by means of a device for moving fluid through the wound and means for fluid cleansing applied to the fluid in recirculation in the fluid recirculation tube upstream of and towards the wound dressing.

The means for flow switching between supply and recirculation may be similarly provided in a form in which concomitant supply and/or recirculation is possible, and to make the necessary adjustments to maintain the desired balance of fluid in recirculation by means of the means for flow switching.

It will be appreciated that where a positive or negative pressure is to be applied to the wound, at least one hollow body in the recirculation flow path to and from the wound bed should have sufficient resilience against the pressure to allow any significant compression or decompression of the irrigant fluid to occur.

In all embodiments of the apparatus, the type and material of such bodies (which are defined by a film, sheet or membrane) that are described by way of example herein to be suitable for use in the present invention will be largely capable of this function.

Thus, examples of suitable materials for bodies defined by a film, sheet or membrane, such as inlet or offtake and/or recirculation tubes and structures such as bags, chambers and pouches, filled with irrigant fluid, are suitably elastically resilient thermoplastic materials that are potentially capable of this function when pressure is applied in this way.

The present invention in this aspect provides several advantages.

One is that application of a positive pressure to the wound under the backing layer may make it possible to flood the tissue underlying the wound with one or more physiologically active components.

This may be effected in therapeutically active amounts, to promote greater wound healing than by treatment with the fluid physiologically active component(s) alone.

Such physiologically active components of the exudate that are beneficial to wound healing may be e.g. be enzymes or other species and may be supplied from the dialysate of a dialytic means for fluid cleansing.

It is believed that using the apparatus for aspirating, irrigating and/or cleansing wounds of the present invention cyclically the effects may be further enhanced.

Circulating wound fluid aids in movement of biological signalling molecules involved in wound healing to locations in the wound bed that are favourable to the wound healing process and/or to cells that would otherwise not be exposed to them, e.g. in a highly exuding wound.

This is especially the case in those embodiments of the apparatus of this first aspect of the present invention for aspirating, irrigating and/or cleansing wounds where there is an inlet or outlet manifold from which tubules radiate and run to the wound bed to end in openings that deliver and collect the fluid directly from the wound bed over an extended area.

Such materials include cytokines, enzymes, nutrients for wound cells to aid proliferation, oxygen, and other molecules that are beneficially involved in wound healing, such as growth factors, and others having beneficial effects (which may be further enhanced) in causing chemotaxis.

The whole length of the apparatus for aspirating, irrigating and/or cleansing wounds should be microbe-impermeable once the wound dressing is over the wound in use.

It is desirable that the wound dressing and the interior of the apparatus for aspirating, irrigating and/or cleansing wounds of the present invention is sterile.

The fluid may be sterilised in the fluid reservoir and/or the rest of the system in which the fluid recirculates, including the means for fluid cleansing, by ultraviolet, gamma or electron beam irradiation. This way, in particular reduces or eliminates contact of internal surfaces and the fluid with any sterilising agent.

Examples of other methods of sterilisation of the fluid also include e.g. the use of ultrafiltration through microapertures or micropores, e.g. of 0.22 to 0.45 micron maximum cross-dimension, to be selectively impermeable to microbes; and fluid antiseptics, such as solutions of chemicals, such as chlorhexidine and povidone iodine; metal ion sources, such as silver salts, e.g. silver nitrate; and hydrogen peroxide;

although the latter involve contact of internal surfaces and the fluid with the sterilising agent.

It may be desirable that the interior of the wound dressing, the rest of the system in which the fluid recirculates, and/or the wound bed, even for a wound in a highly exuding state, are kept sterile after the fluid is sterilised in the fluid reservoir, or that at least naturally occurring microbial growth is inhibited.

Thus, materials that are potentially or actually beneficial in this respect may be added to the irrigant initially, and as desired the amount in recirculation increased by continuing addition.

Examples of such materials include antibacterial agents (some of which are listed above), and antifungal agents. Amongst those that are suitable are, for example triclosan, iodine, metronidazole, cetrimide, chlorhexidine acetate, sodium undecylenate, chlorhexidine and iodine.

Buffering agents, such as potassium dihydrogen phosphate/disodium hydrogen phosphate, may be added to adjust the pH.

Local analgesics/anaesthetics, such as lidocaine/lignocaine hydrochloride, xylocalne (adrenoline, lidocaine) and/or anti-inflammatories may also be added to reduce wound pain or inflammation or pain associated with the dressing.

It is also desirable to provide a system in which physiologically active components of the exudate that are beneficial to wound healing are not removed before or after the application of fluid cleansing, e.g. by the passive deposition of materials that are beneficial in promoting wound healing, such as proteins, e.g. growth factors.

This may occur at any point at least one inlet or outlet pipe through at least one aperture, hole, opening, orifice, slit or slot.

The fluid contained in the hollow body may the deposition of materials that are beneficial in promoting wound healing, and consequent coating,
  a) may be added to the irrigant initially, and as desired the amount in recirculation increased by continuing addition, or
  b) may be used at any point or on any integer in the recirculation path in direct contact with the fluid, e.g. on the means for fluid cleansing or any desired tube or pipe.

Examples of coating materials for surfaces over which the circulating fluid passes include
  anticoagulants, such as heparin, and
  high surface tension materials, such as PTFE, and polyamides,
which are useful for growth factors, enzymes and other proteins and derivatives.

The apparatus of the invention for aspirating, irrigating and/or cleansing wounds is provided with means for admitting fluids directly or indirectly to the wound under the wound dressing in the form of a fluid supply tube to a fluid reservoir.

The fluid reservoir may be of any conventional type, e.g. a tube, bag (such as a bag typically used for blood or blood products, e.g. plasma, or for infusion feeds, e.g. of nutrients), chamber, pouch or other structure, e.g. of polymer film, which can contain the irrigant fluid.

The reservoir may be made of a film, sheet or membrane, often with a (generally uniform) thickness similar to that of films or sheets used in conventional wound dressing backing layers, i.e. up to 100 micron, preferably up to 50 micron, more preferably up to 25 micron, and of 10 micron minimum thickness, and is often a resiliently flexible, e.g. elastomeric, and preferably soft, hollow body.

In all embodiments of the apparatus the type and material of the tubes throughout the apparatus of the invention for aspirating, irrigating and/or cleansing wounds and the fluid reservoir will be largely determined by their function.

To be suitable for use, in particular on chronic timescales, the material should be non-toxic and biocompatible, inert to any active components, as appropriate of the irrigant from the fluid reservoir and/or wound exudate in the apparatus flow path, and, in any use of a two-phase system dialysis unit, of the dialysate that moves into the circulating fluid in the apparatus.

When in contact with irrigant fluid, it should not allow any significant amounts of extractables to diffuse freely out of it in use of the apparatus.

It should be sterilisable by ultraviolet, gamma or electron beam irradiation and/or with fluid antiseptics, such as solutions of chemicals, fluid- and microbe-impermeable once in use, and flexible.

Examples of suitable materials for the fluid reservoir include synthetic polymeric materials, such as polyolefins, such as polyethylene, e.g. high-density polyethylene and polypropylene.

Suitable materials for the present purpose also include copolymers thereof, for example with vinyl acetate and mixtures thereof. Suitable materials for the present purpose further include medical grade poly(vinyl chloride).

Notwithstanding such polymeric materials, the fluid reservoir will often have a stiff area to resist any substantial play between it and components that are not mutually integral, such as the fluid supply tube towards the wound dressing, and may be stiffened, reinforced or otherwise strengthened, e.g. by a projecting boss.

The device for moving fluid through the wound and means for fluid cleansing may be any appropriate for this purpose, and may act at any appropriate point for this purpose.

It may apply a positive or negative pressure to the wound, although its prime purpose is to move fluid (irrigant from the fluid reservoir and/or wound exudate through the length of the apparatus flow path, rather than to apply a positive or negative pressure to the wound.

If applied to the fluid in recirculation in the fluid recirculation tube upstream of and towards the wound dressing and/or the fluid in the fluid supply tube towards the wound dressing (optionally or as necessary via means for flow switching between supply and recirculation), it will usually apply positive pressure (i.e. above-atmospheric pressure) to the wound bed and optionally tissue surrounding the wound.

Often the means for fluid cleansing is (most appropriately for its purpose) downstream of the wound dressing, and provides the highest resistance in the flow path. This is especially the case where the means for fluid cleansing is a single-phase system, e.g. with ultrafiltration through microapertures or micropores, thus enhancing applied positive pressure to the wound.

Where the device is applied to the fluid in recirculation in the fluid recirculation tube and/or the fluid in the fluid offtake tube downstream of and away from the wound dressing, it will usually apply negative pressure (i.e. below-atmospheric pressure or vacuum) to the wound bed and optionally tissue surrounding the wound.

Again, often the means for fluid cleansing is (most appropriately for its purpose) downstream of the wound dressing, and provides the highest resistance in the flow path, thus enhancing applied negative pressure to the wound.

The following types of pump may be used as desired:
reciprocating pumps, such as:
shuttle pumps—with an oscillating shuttle mechanism to move fluids at rates from 2 to 50 ml per minute;
diaphragm pumps—where pulsations of one or two flexible diaphragms displace liquid while check valves control the direction of the fluid flow.
piston pumps—where pistons pump fluids through check valves, in particular for positive and/or negative pressure on the wound bed;
rotary pumps, such as:
centrifugal pumps
flexible impeller pumps—where elastomeric impeller traps fluid between impeller blades and a moulded housing that sweeps fluid through the pump housing.
progressing cavity pumps—with a cooperating screw rotor and stator, in particular for higher-viscosity and particulate-filled exudate;
rotary vane pumps—with rotating vaned disk attached to a drive shaft moving fluid without pulsation as it spins. The outlet can be restricted without damaging the pump.
peristaltic pumps—with peripheral rollers on rotor arms acting on a flexible fluid circulation tube to urge fluid current flow in the tube in the direction of the rotor.

The type and/or capacity of the device will be largely determined by
a) the appropriate or desired fluid volume flow rate of irrigant and/or wound exudate from the wound, and
b) whether it is appropriate or desired to apply a positive or negative pressure to the wound bed, and the level of such pressure to the wound bed
for optimum performance of the wound healing process, and by factors such as portability, power consumption and isolation from contamination.

Such a device may also suitably be one that is capable of pulsed, continuous, variable, reversible and/or automated and/or programmable fluid movement. It may in particular be a pump of any of these types.

In practice, even from a wound in a highly exuding state, such a rate of exudate flow is only of the order of up to 75 microliters/$cm^2$/hr (where $cm^2$ refers to the wound area), and the fluid can be highly mobile (owing to the proteases present). Exudate levels drop and consistency changes as the wound heals, e.g. to a level for the same wound that equates to 12.5-25 microliters/$cm^2$/hr.

Where materials deleterious to wound healing are removed by a two-phase system (see below), such as a dialysis unit, fluid is also potentially lost to the system through the means for fluid cleansing.

This may occur, e.g. through a dialysis polymer film, sheet or membrane which is also permeable to water, in addition to materials deleterious to wound healing.

The balance of fluid in recirculation may thus further decrease, but may be adjusted to minimise this undesired loss in a routine manner as described hereinbefore.

Hence, it will be seen that the circulating fluid from the wound will typically contain a preponderance of irrigant over wound exudate in recirculation from the fluid reservoir.

The type and/or capacity of the device will thus be largely determined in this respect by the appropriate or desired fluid volume flow rate of irrigant, rather than that of exudate, from the wound.

In practice, such a rate of flow of total irrigant and/or wound exudate will be of the order of 1 to 1000, e.g. 3 to 300, and less preferably 1 to 10 ml/cm$^2$/24 hour, where the cm$^2$ refers to the wound area.

The volume of irrigant and/or wound exudate in recirculation may vary over a wide range, but will typically be e.g. 1 to 8 l. (for example for large torso wounds), 200 to 1500 ml (for example for axillary and inguinal, wounds), and 0.3 to 300 ml for limb wounds when the therapy is applied in this way.

In practice, suitable pressures are of the order of up to 25% atm such as up to 10% atm. positive or negative pressure on the wound bed, the apparatus being operated as a closed recirculating system.

The higher end of these ranges are potentially more suitable for hospital use, where relatively high % pressures and/or vacua may be used safely under professional supervision.

The lower end is potentially more suitable for home use, where relatively high % pressures and/or vacua cannot be used safely without professional supervision, or for field hospital use.

The device may be a peristaltic pump or diaphragm pump, e.g. preferably a small portable diaphragm or peristaltic pump. These are preferred types of pump, in order in particular to reduce or eliminate contact of internal surfaces and moving parts of the pump with (chronic) wound exudate, and for ease of cleaning.

It may suitably be one that applies positive pressure to the wound and/or the means for fluid cleansing.

A preferred pump when the applied pressure is positive is a peristaltic pump, e.g. a small, portable peristaltic pump, mounted upstream of the means for fluid cleansing.

Where the pump is a peristaltic pump, this may be e.g. an Instech Model P720 miniature peristaltic pump, with a flow rate: of 0.2-180 ml/hr and a weight of <0.5 k. This is potentially useful for home and field hospital use.

The pump may suitably be one that applies negative pressure to the wound and/or the means for fluid cleansing. A preferred pump when the applied pressure is negative is a diaphragm pump, e.g. a small, portable diaphragm pump, mounted downstream of the dressing or the means for fluid cleansing.

Where the pump is a diaphragm pump, and preferably a small portable diaphragm pump, the one or two flexible diaphragms that displace liquid may each be, for example a polymer film, sheet or membrane, that is connected to means for creating the pulsations. This may be provided in any form that is convenient, inter alia as an electromechanical transducer, a core of a solenoid or a ferromagnetic integer and coil in which the direction of current flow alternates, a rotary cam and follower, and so on.

The outlet from the dressing passes to the means for fluid cleansing for removal of materials deleterious to wound healing from wound exudate, and in turn to the fluid recirculation tube(s).

The apparatus of the invention for aspirating, irrigating and/or cleansing wounds is provided with means for fluid cleansing, which may be
 a) a single-phase system, such as an ultrafiltration unit, or a chemical absorption and/or adsorption unit; or
 b) a two-phase system, such as a dialysis unit, or a biphasic extraction unit.

In the former, circulating fluid from the wound and the fluid reservoir passes through a self-contained system in which materials deleterious to wound healing are removed and the cleansed fluid, still containing materials that are beneficial in promoting wound healing are returned to the wound. The single-phase system may be of any conventional type.

Examples of the means for fluid cleansing in such a system include a macro- or microfiltration unit, which appropriately comprises one or more macroscopic and/or microscopic filters.

These are to retain particulates, e.g. cell debris and micro-organisms, allowing proteins and nutrients to pass through.

Alternatively, they also include an ultrafiltration unit, such as a one in which the cleansing integer is a filter for materials deleterious to wound healing, for example a high throughput, low protein-binding polymer film, sheet or membrane which is selectively impermeable to materials deleterious to wound healing, which are removed and the cleansed fluid, still containing materials that are beneficial in promoting wound healing is passed by it.

The membrane may preferably be of a hydrophilic polymeric material, such as a cellulose acetate—nitrate mixture, polyvinylidene chloride, and, for example hydrophilic polyurethane.

Examples of less preferred materials include hydrophobic materials also including polyesters, such as polycarbonates, PTFE, and polyamides, e.g. 6-6 and 6-10, and hydrophobic polyurethanes, and quartz and glass fibre.

It has microapertures or micropores, the maximum cross-dimension of which will largely depend on the species that are to be selectively removed in this way and those to which it is to be permeable.

The former may be removed with microapertures or micropores, e.g. typically with a maximum cross-dimension in the range of 20 to 700 micron, e.g. 20 to 50 nm (for example for undesired proteins), 50 to 100 nm, 100 to 250 nm, 250 to 500 nm and 500 to 700 nm.

The filter integer may be a flat sheet or a membrane of a polymeric material in a more convoluted form, e.g. in the form of elongate structure, such as pipes, tubules, etc.

The system may be a chemical adsorption unit, for example one in which a particulate, such as a zeolite, or a layer, e.g. of a functionalised polymer has sites on its surface that are capable of removing materials deleterious to wound healing on passing the circulating fluid from the wound and the fluid reservoir over them.

The materials may be removed, e.g. by destroying or binding the materials that are deleterious to wound healing, by, for example chelators and/or ion exchangers, degraders, which may be enzymes.

Examples of such also include less specific chemical adsorption units, for example one in which a physical absorbent, such as activated carbon or a zeolite, has non-specific sites on its surface that are capable of removing materials deleterious to wound healing on passing the circulating fluid from the wound and the fluid reservoir over them.

The cleansing integer, for example the polymer film, sheet or other chemical absorption and/or adsorption means, etc should of course be capable of removing materials deleterious to wound healing at a practical rate for a given capacity of the apparatus flow path and the flow rate of irrigant.

In the two-phase system, circulating fluid from the wound and the fluid reservoir in indirect or (less usually, direct) contact with a second fluid (dialysate) phase, more usually a liquid.

Thus, in one form, a biphasic liquid extraction unit, the second fluid phase is (usually) a liquid that is immiscible with the circulating fluid from the dressing, over a surface of which the circulating fluid passes in direct contact with the cleansing fluid. Materials deleterious to wound healing are removed into the dialysate, and the cleansed fluid, still containing materials that are beneficial in promoting wound healing, is returned via the recirculation tube to the wound bed.

Examples of such means for fluid cleansing include those wherein the second fluid (dialysate) phase is perfluorodecalin and like materials Alternatively, where appropriate it may be provided in a form in which the two fluids (recirculation fluid and dialysate) are separated by a significantly two-dimensional integer, for example a polymer film, sheet or membrane or hollow fibre or filament that is permeable to materials in the circulating fluid in the apparatus.

Again, materials deleterious to wound healing are removed into the dialysate, and the cleansed fluid, still containing materials that are beneficial in promoting wound healing, is returned via the recirculation tube to the wound bed.

In either form in which the two-phase system, such as a dialysis unit, is provided, in use typically the dialysate moves past the circulating fluid in the apparatus in a co- or preferably counter-current direction.

Pumps, such as peristaltic pumps, and/or valves control the direction of the two fluid flows.

However, the cleansing fluid may less usually be static, although this may not provide a system with sufficient (dynamic) surface area to remove materials deleterious to wound healing from wound exudate at a practical rate.

Typical dialysate flow rates in a dialytic means for fluid cleansing in the present apparatus for aspirating, irrigating and/or cleansing wounds are those used in the conventional type of two-phase system, such as a dialysis unit for systemic therapy.

The integer may be a film, sheet or membrane, often of the same type, and of the same (generally uniform) thickness, as those used in conventional two-phase system, such as a dialysis unit for systemic therapy.

The film, sheet or membrane may be substantially flat, and depending on any pressure differential across it may require other materials on or in it to stiffen, reinforce or otherwise strengthen it.

However, this may not provide a system with sufficient functional surface area to remove materials deleterious to wound healing from wound exudate at a practical rate.

To be suitable for use, in particular in chronic wound dialysis, with relatively high concentrations of materials that are deleterious to wound healing, it may be advantageous to provide a system in which the film, sheet or membrane of a polymeric material is in a more convoluted form.

This may be in the form of elongate structures, such as pipes, tubes hollow fibres or filaments or tubules of a round cross-section, e.g. elliptical or circular, e.g. in a parallel array with spaces therebetween.

The wound irrigant and/or wound exudate may recirculate through the inside and the cleansing fluid may pass into the spaces between adjacent pipes, tubes or tubules in a co- or preferably counter-current direction, or vice versa.

Again, materials deleterious to wound healing are removed into the dialysate, and the cleansed fluid, still containing materials that are beneficial in promoting wound healing, is returned via the recirculation tube to the wound.

Where the means for fluid cleansing is a two-phase system, e.g. in the form of a dialysis unit, or a biphasic extraction unit, the circulating fluid from the wound and the fluid reservoir passes across one surfaces of a significantly two-dimensional integer, for example a polymer film, sheet or membrane which is selectively permeable to materials deleterious to wound healing.

These are removed by passing a cleansing fluid across the other surface of the integer. The integer may be a film, sheet or membrane that is selectively permeable to the foregoing materials deleterious to wound healing.

Examples of these as above include oxidants, such as free radicals, e.g. peroxide and superoxide;

iron II and iron III;

all involved in oxidative stress on the wound bed;

proteases, such as serine proteases, e.g. elastase and thrombin; cysteine proteases; matrix metalloproteases, e.g. collagenase; and carboxyl (acid) proteases;

endotoxins, such as lipopolysaccharides;

bacterial autoinducer signalling molecules, such as homoserine lactone derivatives, e.g. oxo-alkyl derivatives;

inhibitors of angiogenesis such as thrombospondin-1 (TSP-1), plasminogen activator inhibitor, or angiostatin (plasminogen fragment);

pro-inflammatory cytokines such as tumour necrosis factor alpha (TNF$\alpha$) and interleukin 1 beta (IL-$\beta$), and inflammatories, such as lipopolysaccharides, and e.g. histamine.

Examples of suitable materials for the film, sheet or membrane (typically in the form of conformable hollow bodies defined by the film, sheet or membrane, such as the structures described hereinbefore) include natural and synthetic polymeric materials.

The membrane may be of one or more hydrophilic polymeric materials, such as a cellulose derivative, e.g. regenerated cellulose, a cellulose mono-, di- or tri-esters, such as cellulose mono-, di- or tri-acetate, benzyl cellulose and Hemophan, and mixtures thereof.

Examples of other materials include hydrophobic materials, such as aromatic polysulphones, polyethersulphones, polyetherether-sulphones, polyketones, polyetherketones and polyetherether-ketones, and sulphonated derivatives thereof, and mixtures thereof.

Examples of other materials include hydrophobic materials, such as polyesters, such as polycarbonates and polyamides, e.g. 6-6 and 6-10; polyacrylates, including, e.g. poly(methyl methacrylate), polyacrylonitrile and copolymers thereof, for example acrylonitrile-sodium metallosulphonate copolymers; and poly(vinylidene chloride).

Suitable materials for the present membranes include thermoplastic polyolefins, such as polyethylene e.g. high-density polyethylene, polypropylene, copolymers thereof, for example with vinyl acetate and polyvinyl alcohol, and mixtures thereof.

The dialysis membrane should have a molecular weight cut off (MWCO) chosen to allow selective perfusion of species deleterious to wound healing that have been targeted for removal from the wound. For example, perfusion of the serine protease elastase (molecular weight 25900 Dalton) would require a membrane with MWCO>25900 Dalton. The MWCO threshold can be varied to suit each application between 1 and 3000000 Dalton.

Preferably, the MWCO should be as close as possible to this weight to exclude interference by larger competitor species.

For example, such a membrane with MWCO>25900 Dalton does not allow any significant amounts of the antagonist to elastase, alpha-1-antitrypsin (AAT) (molecular weight 54000 Dalton), which occurs naturally in wounds, to diffuse freely out of the wound fluid into the dialysate.

The inhibitor, which is beneficial in promoting chronic wound healing, remains in contact with the wound bed, and can act beneficially on it, whilst the elastase that is deleterious to wound healing is removed.

Such use of the present apparatus is, e.g. favourable to the wound healing process in chronic wounds, such as diabetic foot ulcers, and especially decubitus pressure ulcers.

As noted hereinafter, antagonists, for example degrading enzymes, or sequestrating agents for elastase on the dialysate side of the membrane, may be used to enhance the removal of this protease from wound exudate.

Where it is desired to remove several different materials that are deleterious to wound healing, it may be advantageous to provide a system of modules in series, each of which removes a different material.

This allows incompatible cleansing materials to be used on the same fluid and/or wound exudates.

Preferably any such system is a conventional automated, programmable system which can cleanse the wound irrigant and/or wound exudate with minimal supervision.

As noted above in more detail, fluid passes from a cleansing fluid through a selectively permeable integer.

This may be the typical permeable polymer film, sheet or membrane of a two-phase system, such as a dialysis unit.

Additionally, solutes or disperse phase species will pass from the dialysate into the irrigant and/or wound exudate through the dialysis polymer film, sheet or membrane.

This property may be used to perfuse materials beneficial to wound healing into the irrigant and/or exudate from a dialysate.

In this less conventional type of infusion feed, a broad spectrum of species will usually pass into the exudate and/or irrigant fluid from the dialysate.

These include ionic species, such as bicarbonate;

vitamins, such as ascorbic acid (vitamin C) and vitamin E, and stable derivatives thereof, and mixtures thereof; to relieve oxidative stress on the wound bed;

pH buffering agents, such as potassium dihydrogen phosphate/disodium hydrogen phosphate, local analgesics/anaesthetics, such as lidocaine/lignocaine hydrochloride and xylocalne (adrenoline lidocaine) and/or anti-inflammatories, to reduce wound pain or inflammation or pain associated with the dressing nutrients to aid proliferation of wound cells, such as amino acids, sugars, low molecular weight tissue building blocks and trace elements; and other cell culture medium species; and gases, such as air, nitrogen, oxygen and/or nitric oxide.

For the purposes of fluid cleansing in the apparatus of the present invention, both the single-phase system, such as an ultrafiltration unit, and two-phase system, such as a dialysis unit, may have captive (non-labile, insoluble and/or immobilised) species such as the following, bound to an insoluble and/or immobilised substrate over and/or through which the irrigant and/or wound exudate from, the wound dressing passes in turn to the fluid recirculation tube(s):

antioxidants and free radical scavengers, such as 3-hydroxytyramine (dopamine), ascorbic acid (vitamin C), vitamin E and glutathione, and stable derivatives thereof, and mixtures thereof; to relieve oxidative stress on the wound bed;

metal ion chelators and/or ion exchangers, such as transition metal ion chelators, such as iron III chelators (Fe III is involved in oxidative stress on the wound bed), such as desferrioxamine (DFO), 3-hydroxytyramine (dopamine), iron III reductants;

protease inhibitors, such as TIMPs and alpha 1-antitrypsin (AAT); serine protease inhibitors, such as 4-(2-aminoethyl)-benzene sulphonyl fluoride (AEBSF, PefaBloc) and N$\alpha$-p-tosyl-L-lysine chloro-methyl ketone (TLCK) and $\epsilon$-aminocaproyl-p-chlorobenzylamide; cysteine protease inhibitors; matrix metalloprotease inhibitors; and carboxyl (acid) protease inhibitors;

sacrificial redox materials that are potentially or actually beneficial in promoting wound healing, by the removal of materials that trigger the expression into wound exudate of redox-sensitive genes that are deleterious to wound healing;

autoinducer signalling molecule degraders, which may be enzymes; and anti-inflammatory materials to bind or destroy lipopolysaccharides, e.g. peptidomimetics Other physiologically active components of the exudate that are deleterious to wound healing may be removed in this way.

These may be removed with suitable chelators and/or ion exchangers, degraders, which may be enzymes, or other species.

The following types of functionalised substrate has sites on its surface that are capable of removing materials deleterious to wound healing on passing the circulating fluid from the wound and the fluid reservoir over them:

heterogeneous resins, for example silica-supported reagents such as: metal scavengers, 3-(diethylenetriamino)propyl-functionalised silica gel 2-(4-(ethylenediamino)benzene)ethyl-functionalised silica gel 3-(mercapto)propyl-functionalised silica gel 3-(1-thioureido)propyl-functionalised silica gel triamine tetraacetate-functionalised silica gel or electrophilic scavengers, 4-carboxybutyl-functionalised silica gel 4-ethyl benzenesulfonyl chloride-functionalised silica gel propionyl chloride-functionalised silica gel 3-(isocyano)propyl-functionalised silica gel 3-(thiocyano)propyl-functionalised silica gel 3-(2-succinic anhydride)propyl-functionalised silica gel 3-(maleimido)propyl-functionalised silica gel or nucleophilic scavengers, 3-aminopropyl-functionalised silica gel 3-(ethylenediamino)-functionalised silica gel 2-(4-(ethylenediamino)propyl-functionalised silica gel 3-(diethylenetriamino)propyl-functionalised silica gel 4-ethyl-benzenesulfonamide-functionalised silica gel 2-(4-toluenesulfonyl hydrazino)ethyl-functionalised silica gel 3-(mercapto)propyl-functionalised silica gel dimethylsiloxy-functionalised silica gel or base or acid scavengers, 3-(dimethylamino)propyl-functionalised silica gel 3-(1,3,4,6,7,8-hexahydro-2H-pyrimido-[1,2-$\alpha$]pyrimidino) propyl-functionalised silica gel 3-(1-imidazol-1-yl)propyl-functionalised silica gel 3-(1-morpholino)propyl-functionalised silica gel 3-(1-piperazino)propyl-functionalised silica gel
3-(1-piperidino)propyl-functionalised silica gel
3-(4,4'-trimethyldipiperidino)propyl-functionalised silica gel
2-(2-pyridyl)ethyl-functionalised silica gel
3-(trimethylammonium)propyl-functionalised silica gel
or the reagents,
3-(1-cyclohexylcarbodiimido)propyl-functionalised silica gel
TEMPO-functionalised silica gel
2-(diphenylphosphino)ethyl-functionalised silica gel
2-(3,4-cyclohexyldiol)propyl-functionalised silica gel
3-(glycidoxy)propyl-functionalised silica gel
2-(3,4-epoxycyclohexyl)propyl-functionalised silica gel
1-(allyl)methyl-functionalised silica gel
4-bromopropyl-functionalised silica gel
4-bromophenyl-functionalised silica gel
3-chloropropyl-functionalised silica gel
4-benzyl chloride-functionalised silica gel
2-(carbomethoxy)propyl-functionalised silica gel
3-(4-nitrobenzamido)propyl-functionalised silica gel
3-(ureido)propyl-functionalised silica gel
or any combinations of the above.

The use of such captive (non-labile, insoluble and/or immobilised) species, such as the foregoing, bound to an insoluble and immobilised) substrate over and/or through which the irrigant and/or wound exudate from, the wound dressing passes has been described hereinbefore as suitable for the means for fluid cleansing.

However, they may additionally, where appropriate, be used in any part of the apparatus that is in contact with the irrigant and/or wound exudate, but often within the dressing, for removal of materials deleterious to wound healing from wound.

A backing layer in the wound dressing with ribs or ridges may be used to assist in channeling fluid across a larger area over a longer dwell time, and hence improve the cleansing of the irrigant in the wound dressing.

The means for fluid cleansing may additionally, where appropriate, comprise one or more macroscopic and/or microscopic filters.

These are to retain particulates, e.g. cell debris and micro-organisms, allowing proteins and nutrients to pass through.

Alternatively, a less conventional type of two-phase system (see above), such as a dialysis unit, may be used as the means for fluid cleansing. In this type, the dialysis polymer film, sheet or membrane is not an integer selectively permeable to materials deleterious to wound healing, such as proteases, such as serine proteases, e.g. elastase and thrombin; cysteine protease; matrix metalloproteases, e.g. collagenase; and carboxyl (acid) proteases;

endotoxins, such as lipopolysaccharides;

inhibitors of angiogenesis such as thrombospondin-1 (TSP-1), plasminogen activator inhibitor, or angiostatin (plasminogen fragment)

pro-inflammatory cytokines such as tumour necrosis factor alpha (TNFα) and interleukin 1 beta (IL-β);

oxidants, such as free radicals, e.g., peroxide and superoxide; and metal ions, e.g. iron II and iron III; all involved in oxidative stress on the wound bed.

It will however also permit components of the exudate from a wound and/or irrigant fluid that may be larger or smaller molecules, but are beneficially involved in wound healing to pass into and through it.

In the dialysate, or preferably in one or more solid structural integers with at least one surface in contact with the dialysate, in the means for fluid cleansing, there are one or more materials that can remove materials deleterious to wound healing from wound exudate, by being antagonists to such species, for example enzymes or others, such as protease inhibitors, such as serine protease inhibitors, such as 4-(2-aminoethyl)-benzene sulphonyl fluoride (AEBSF, PefaBloc) and Nα-p-tosyl-L-lysine chloromethyl ketone (TLCK) and ε-aminocaproyl-p-chlorobenzylamide; cysteine protease inhibitors; matrix metalloprotease inhibitors; and carboxyl (acid) protease inhibitors;

binders and/or degraders, such as anti-inflammatory materials to bind or destroy lipopolysaccharides, e.g. peptidomimetics;

anti-oxidants, such as 3-hydroxytyramine (dopamine), ascorbic acid (vitamin C), vitamin E and glutathione, and stable derivatives thereof, and mixtures thereof; to relieve oxidative stress on the wound bed; and chelators and/or ion exchanges, such as desferrioxamine (DFO), 3-hydroxytyramine (dopamine).

They further include peptides (including cytokines, e.g. bacterial cytokines, such as α-amino-γ-butyrolactone and L-homocarnosine); and sacrificial redox materials that are potentially or actually beneficial in promoting wound healing, such as iron III reductants; and/or regeneratable materials of this type, such as glutathione redox systems; and other physiologically active components.

In use of the two-phase system dialysis unit, of this less conventional type, a broad spectrum of species will usually pass into the dialysate from the exudate.

Some (mainly ionic) species will pass from the dialysate into the irrigant and/or wound exudate through the dialysis polymer film, sheet or membrane that is not very selectively permeable to materials deleterious to wound healing.

The components of the exudate from a wound and/or irrigant fluid will diffuse freely to and fro through it.

If (preferably) none of the dialysate is voided to waste, e.g. to a collection bag, a steady state concentration equilibrium is eventually set up between the dialysate and the irrigant and/or wound exudate, which is 'topped up' from the wound dressing.

Circulating wound fluid aids in the quicker attainment of this equilibrium of materials beneficial in promoting wound healing.

It also returns them to the site where they can be potentially of most benefit, i.e. the wound bed.

The target materials deleterious to wound healing also pass into the dialysate from the exudate through the dialysis polymer film, sheet or membrane that is not very selectively permeable to materials deleterious to wound healing.

Unlike the other components of the exudate from a wound and/or irrigant fluid, the target materials deleterious to wound healing come into contact with the dialysate, or preferably with one or more solid structural integers with at least one surface in the dialysate, and are removed by the appropriate antagonists, binders and/or degraders, chelators and/or ion exchangers and redox agents, etc. The cleansed fluid, still containing some materials that are beneficial in promoting wound healing, is returned to the recirculation tube.

Unlike the other components of the exudate from a wound and/or irrigant fluid the target materials are constantly removed from the dialysate.

Very little of these species will pass from the dialysate into the irrigant and/or wound exudate, and a steady state concentration equilibrium is not set up, even if the species are constantly 'topped up' from the wound dressing.

It is believed that circulating wound fluid aids in removal from recirculation of the materials deleterious to wound healing from wound exudate, whilst retaining materials that are beneficial in promoting wound healing in contact with the wound.

A particular advantage of this form of the two-phase system, is that where a material that can remove materials deleterious to wound healing from wound exudate is (cyto) toxic or bioincompatible, or not inert to any components that are beneficial in promoting wound healing, the system does not allow any significant amounts of antagonist to diffuse freely out of the dialysate into the irrigant fluid. The active material can act beneficially on the fluid however.

The film sheet or membrane is preferably a dialysis membrane of molecular weight cut off (MWCO) (as conventionally defined) chosen to allow perfusion of species targeted for sequestration or destruction.

For example, sequestration of the serine protease elastase (molecular weight 25900 Dalton) would require a membrane with MWCO>25900 Dalton.

The MWCO threshold can be varied to suit each application between 1 and 3000000 Dalton. Preferably, the MWCO should be as close as possible to this weight to exclude sequestering interference by larger competitor species.

Both the single-phase system, such as an ultrafiltration unit, and two-phase system, such as a dialysis unit, may be in modular form that is relatively easily demountable from the apparatus of the invention. The system may suitably comprise one or more such modules.

The conduits through which respectively
a) the irrigant and/or wound exudate passes from the wound dressing and
b) the cleansed fluid, still containing materials that are beneficial in promoting wound healing, is returned to the recirculation tube, and
c) (in the case where the means is provided in the form of a two-phase system, such as an dialysis unit) through which the cleansing fluid enters and exits the means
preferably have means for, on module disconnection and withdrawal,
i) switching off the flow and
ii) providing an immediate fluid-tight seal or closure over the ends of the conduits and the cooperating tubes in the rest of the apparatus of the invention so exposed,
to prevent continuing passage of irrigant and/or exudate and cleansed fluid, and cleansing fluid.

The apparatus of the invention for aspirating, irrigating and/or cleansing wounds is provided with means for bleeding the offtake and/or recirculation tubes, such as a regulator, such as a valve or other control device for bleeding fluids from the wound.

The device for moving fluid through the wound and means for fluid cleansing is used to move irrigant to the wound dressing and apply the desired positive or negative pressure on the wound bed.

The desired balance of fluid in recirculation tube will typically be regulated by means of
a) the means for bleeding the offtake and/or recirculation tubes,
b) the means for flow switching between supply and recirculation, and/or
c) the means for moving fluid over the wound bed and through the means for fluid cleansing,
as appropriate.

Thus, e.g. if
a) the apparatus for aspirating, irrigating and/or cleansing wounds is a single-phase system, such as an ultrafiltration unit,
b) the wound is not in a highly exuding state and
c) it is not appropriate or desired to admit fluid into the wound from the fluid reservoir,
there is no or negligible change in the balance of fluid in recirculation.

Once it has been primed throughout, e.g. to the desired positive or negative pressure on the wound bed, the apparatus may be operated as a closed recirculating system.

The means for flow switching between supply and recirculation tubes is set to close the wound to the fluid reservoir via the fluid supply tube, and the means for bleeding the offtake and/or recirculation tubes are also closed.

If
a) the apparatus for aspirating, irrigating and/or cleansing wounds is a single-phase system, such as an ultrafiltration unit,
b) the wound is in a highly exuding state and/or
c) it is appropriate or desired to admit fluid into the wound from the fluid reservoir,
there is a positive change in the balance of fluid in recirculation.

Once it has been primed throughout, e.g. to the desired positive or negative pressure on the wound bed, the apparatus cannot be operated as a closed recirculating system, without the pressure to the wound bed increasing, possibly undesirably.

The means for bleeding the offtake and/or recirculation tubes must be opened to some extent to relieve positive pressure on the wound bed. The bleed-off may be voided to waste, e.g. to a collection bag.

Materials that are beneficial in promoting wound healing may be lost to the site where they can be potentially of most benefit, i.e. the wound bed, when the therapy is applied in this way.

However, the balance of fluid in recirculation may be routinely adjusted to minimise this undesired loss.

The factors that determine the balance of fluid in recirculation in an apparatus with a two-phase system means for fluid cleansing in the form of a dialysis unit, or a biphasic extraction unit have been described hereinbefore in detail hereinbefore.

It is sufficient to note here that at some point after steady state recirculation established through the length of the apparatus flow path, it may be necessary that any bleed valve is opened, if overall the fluid level is increasing by transfer from the dialysate to an undesirable extent.

Other combinations, and the necessary adjustments to maintain the desired balance of fluid in recirculation tube by means of
a) the means for bleeding the offtake and/or recirculation tubes,
b) the means for flow switching between supply and recirculation, and/or
c) the means for moving fluid
will be apparent to the ski lied person.

The outlet from the means for bleeding the offtake and/or recirculation tubes may be collected and monitored and used to diagnose the status of the wound and/or its exudate.

The waste reservoir may be of any conventional type, e.g. a tube, bag (such as a bag typically used as an ostomy bag), chamber, pouch or other structure, e.g. of polymer film, which can contain the irrigant fluid that has been bled off. In all embodiments of the apparatus, the type and material of the waste reservoir will be largely determined by its function. To be suitable for use, the material need only be fluid-impermeable once in use, and flexible.

Examples of suitable materials for the fluid reservoir include synthetic polymeric materials, such as polyolefins, such as poly (vinylidene chloride).

Suitable materials for the present purpose also include polyethylene, e.g. high-density polyethylene, polypropylene, copolymers thereof, for example with vinyl acetate and mixtures thereof.

In a second aspect of the present invention there is provided a conformable wound dressing, characterised in that it comprises a backing layer with a wound-facing face which is capable of forming a relatively fluid-tight seal or closure over a wound and has at least one inlet pipe for connection to a fluid supply tube, which passes through and/or under the wound-facing face, and at least one outlet pipe for connection to a fluid offtake tube, which passes through and/or under the wound-facing face, the point at which the or each inlet pipe and the or each outlet pipe passes through and/or under the wound-facing face forming a relatively fluid-tight seal or closure over the wound; and means for applying stress to the wound bed and optionally the tissue surrounding the wound.

The dressing is advantageously provided for use in a bacteria-proof pouch. Examples of suitable forms of such wound dressings are as described by way of example hereinbefore.

It is an object of the present invention c) to obviate at least some of the disadvantages of known aspiration and/or irrigation therapies, and
d) to provide a system of therapy which
  i) can remove materials deleterious to wound healing from wound exudate, whilst retaining materials that are beneficial in promoting wound healing in contact with the wound bed, and/or
  ii) which allows fluids containing active amounts of materials that are beneficial in promoting wound healing to pass into and/or through the wound in contact with the wound bed.

Thus, in a third aspect of the present invention there is provided a method of treating wounds to promote wound healing using the apparatus for aspirating, irrigating and/or cleansing wounds of the present invention.

BRIEF DESCRIPTION OF THE DRAWINGS

The present invention will now be described by way of example only with reference to the accompanying drawings in which:

FIG. 1b is a cross-sectional side view of the wound dressing portion of the apparatus of FIG. 1a.

It has a single-phase system means for fluid cleansing in the form of an ultrafiltration unit.

The dressing in the apparatus is shown schematically with the means for applying stress to the wound bed omitted for clarity.

Figure 2:
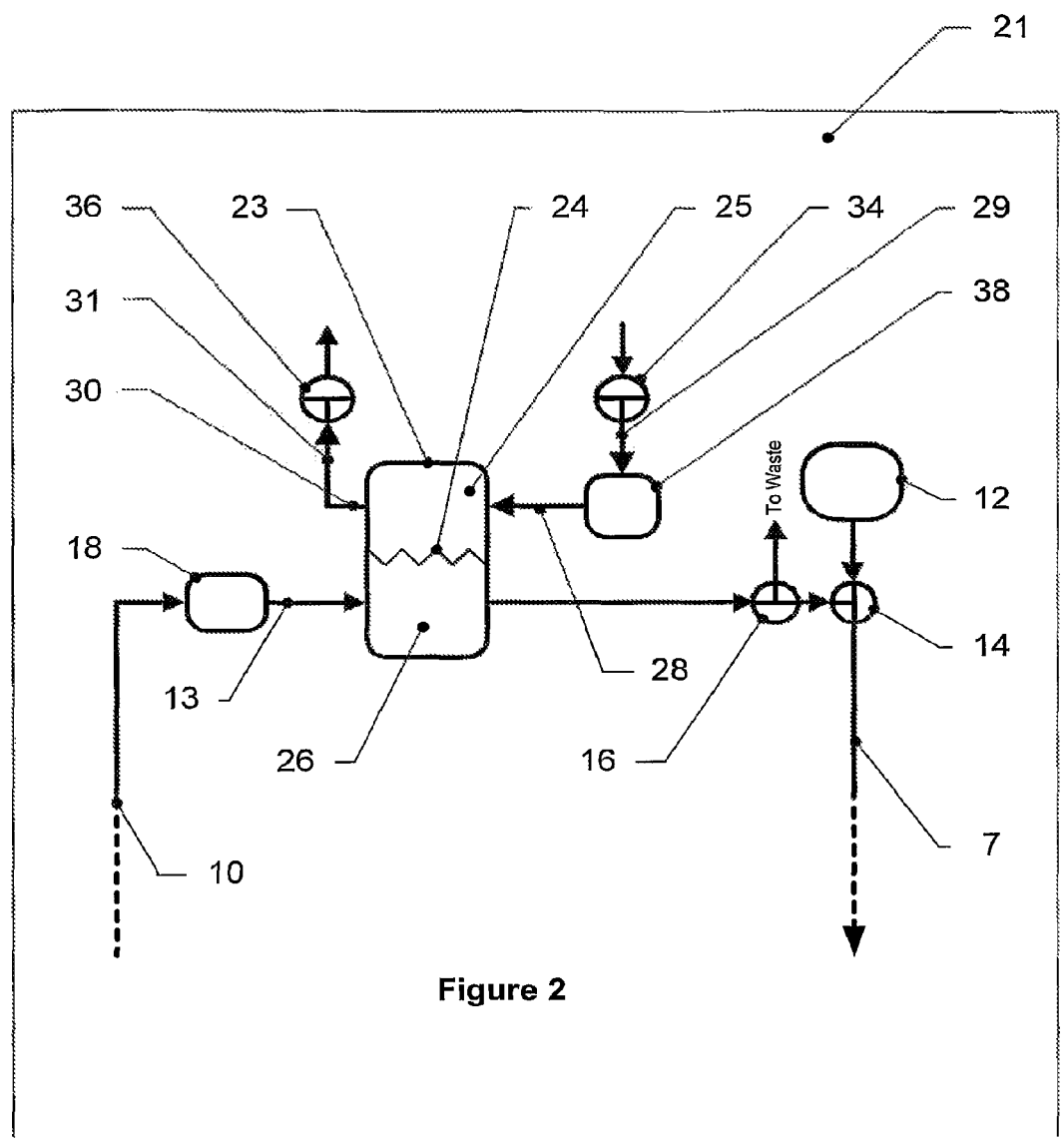

FIG. 2 is a schematic view of an apparatus for aspirating, irrigating and/or cleansing a wound according to the first aspect of the present invention.

It has a two-phase system means for fluid cleansing in the form of a dialysis unit, or a biphasic extraction unit.

FIGS. 3a to 8b are views of conformable wound dressings, of the second aspect of the present invention for aspirating and/or irrigating wounds.

Figure 3A:
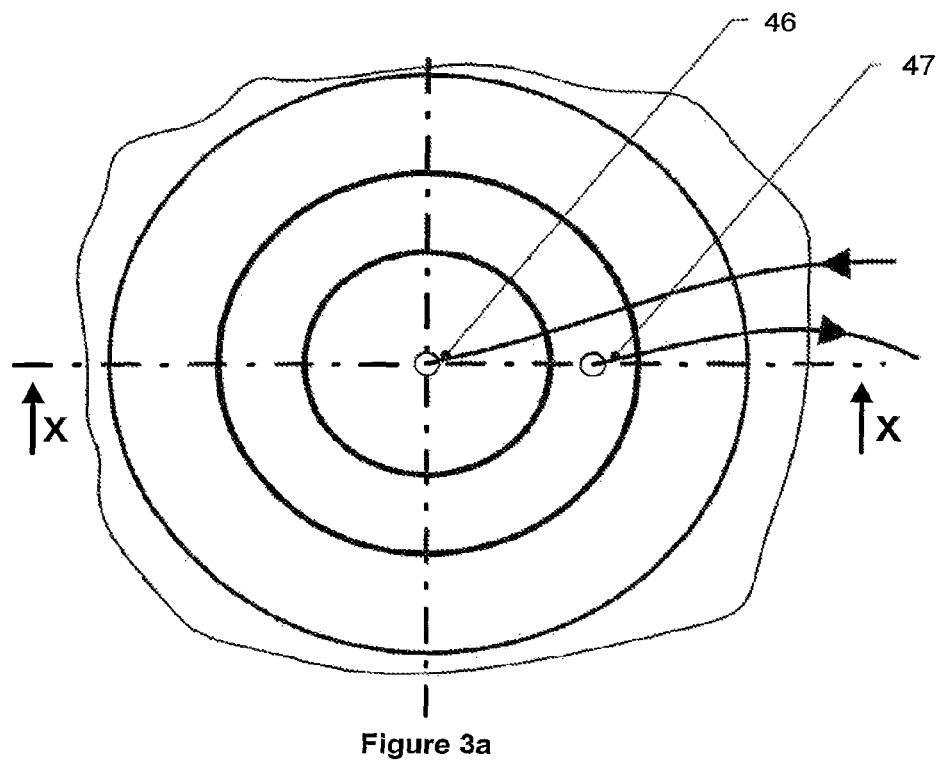
Figure 3B:
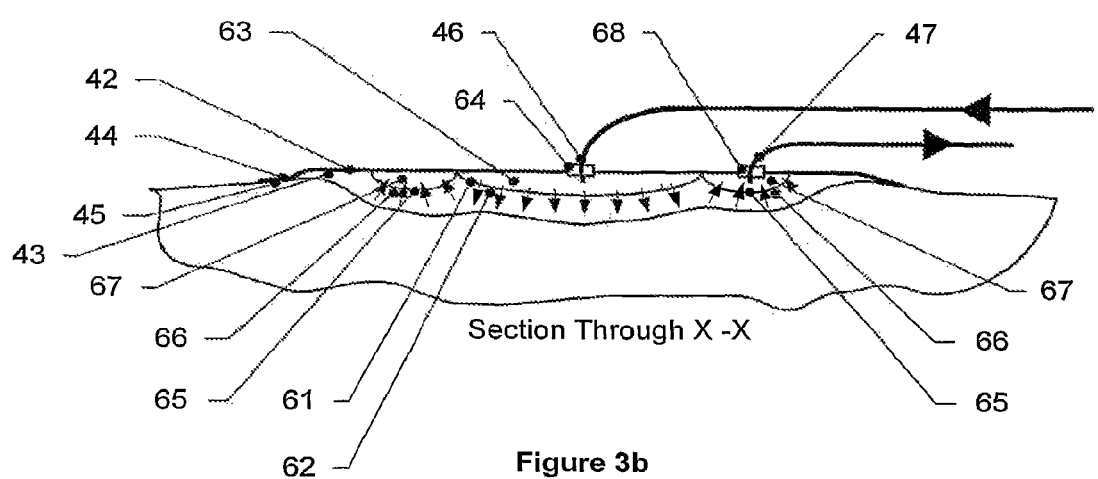
Figure 4A:
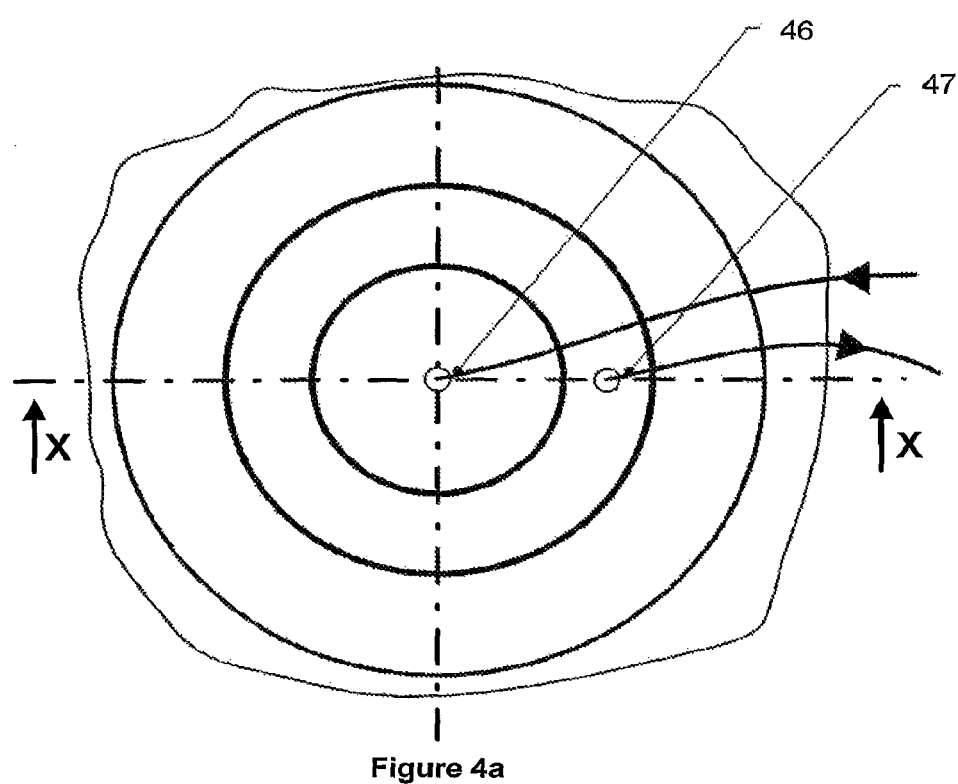
Figure 4B:
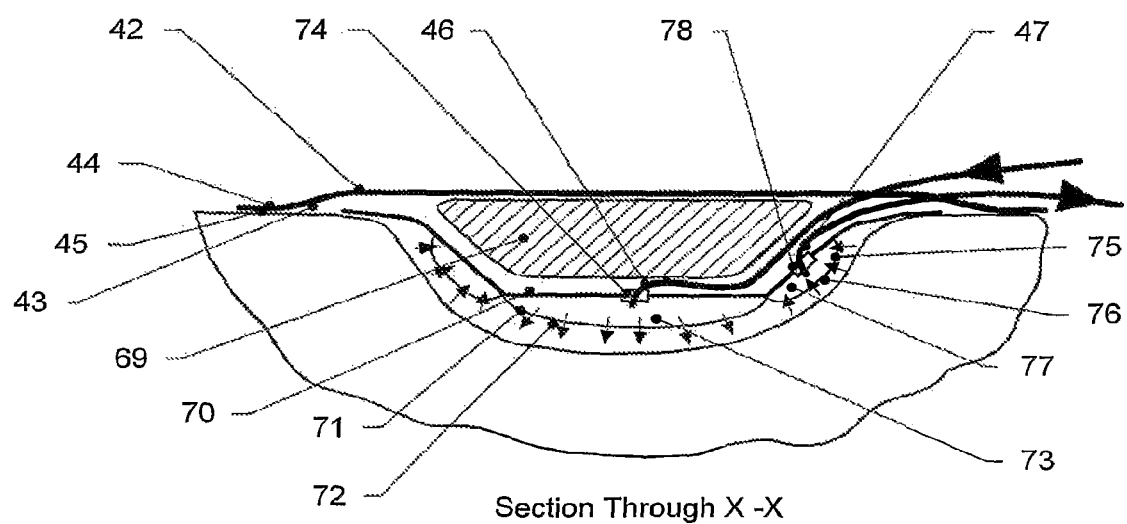
Figure 5A:
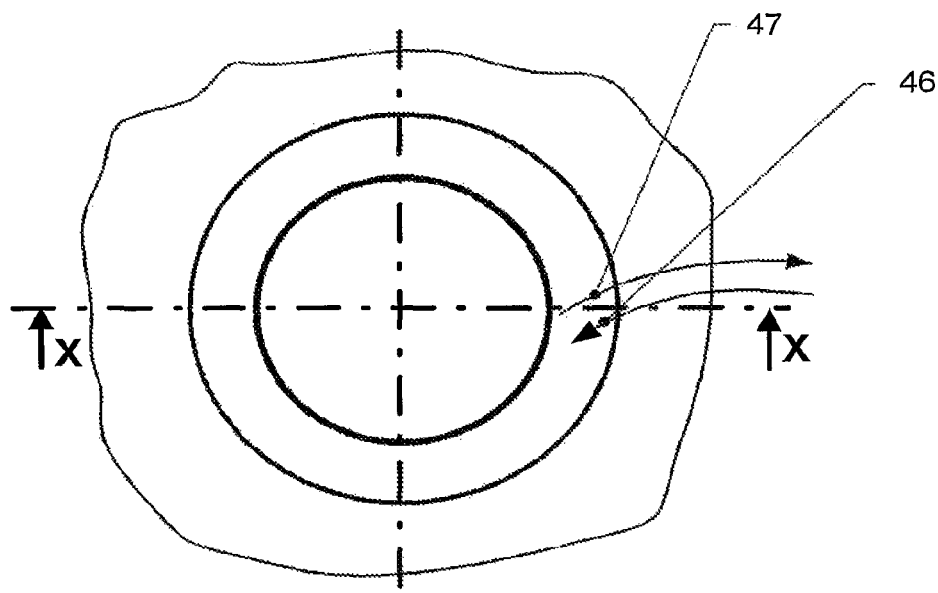

In these, FIGS. 3a, 4a, and 5a are plan views of the wound dressings, and FIGS. 3b, 4b, 5b, 6, 7 and 8a are cross-sectional side views of the wound dressings.

Figure 8A:
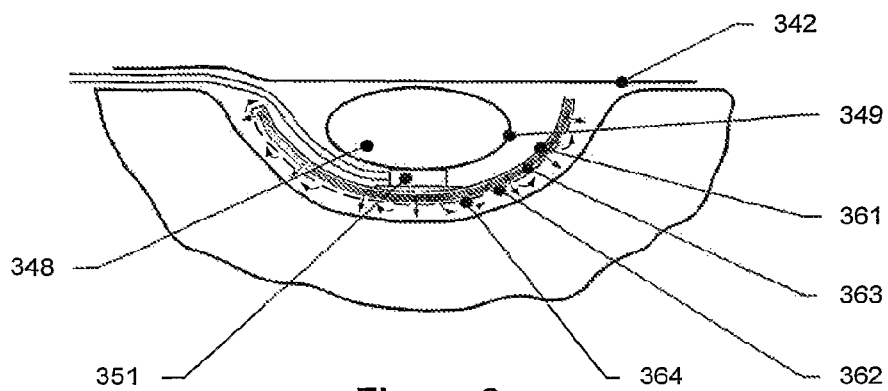
Figure 8B:
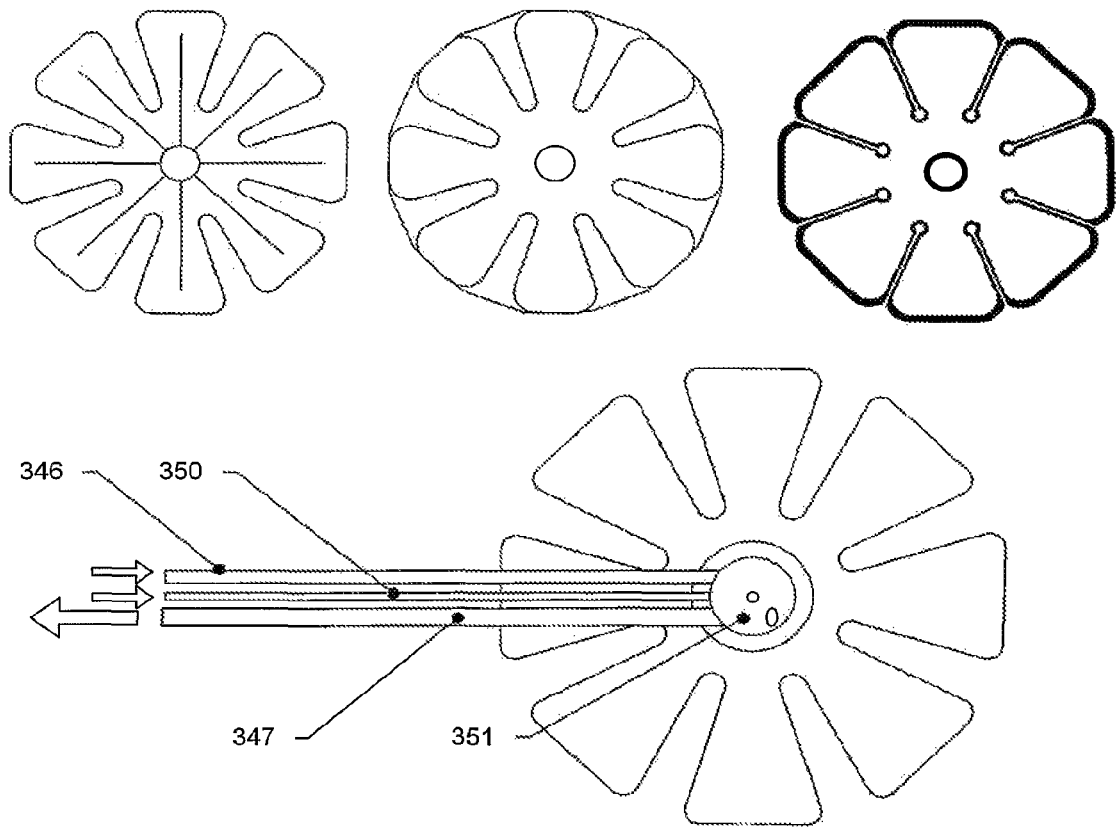

FIG. 8b is a plan view of embodiments of a chamber.

Figure 9A:
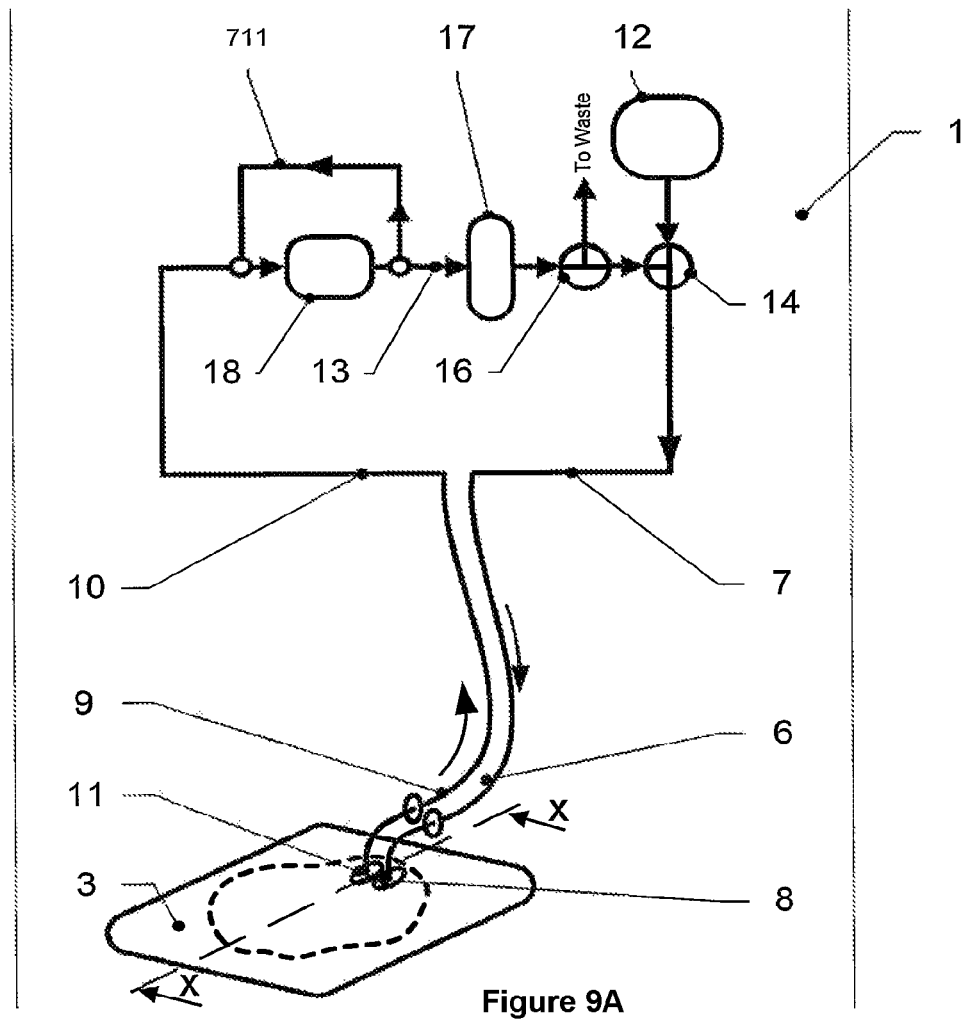
Figure 9B:
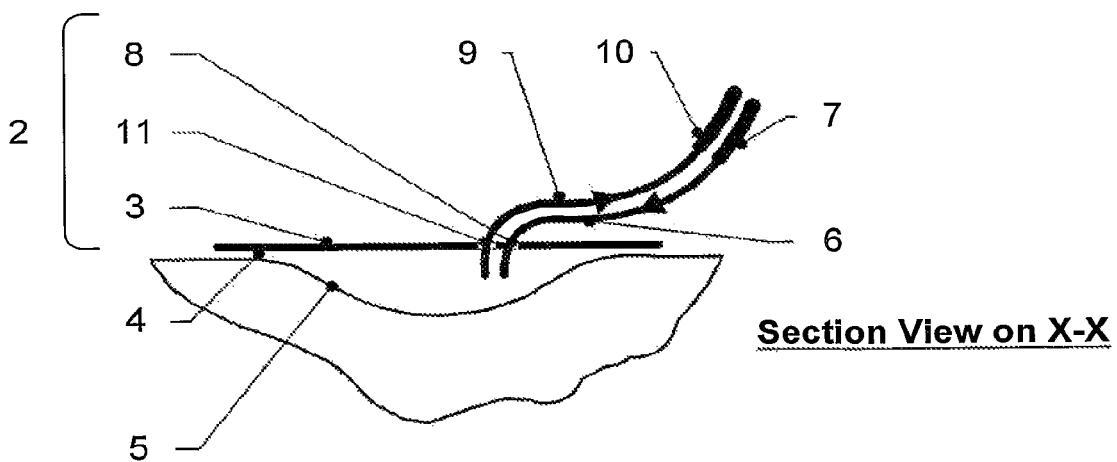

FIG. 9a is a schematic view of an apparatus for aspirating, irrigating and/or cleansing a wound according to the first aspect of the present invention. It has a single-phase system means for fluid cleansing in the form of an ultrafiltration unit. FIG. 9b is a cross-sectional side view of the wound dressing portion of the apparatus of FIG. 9a.

Figure 10:
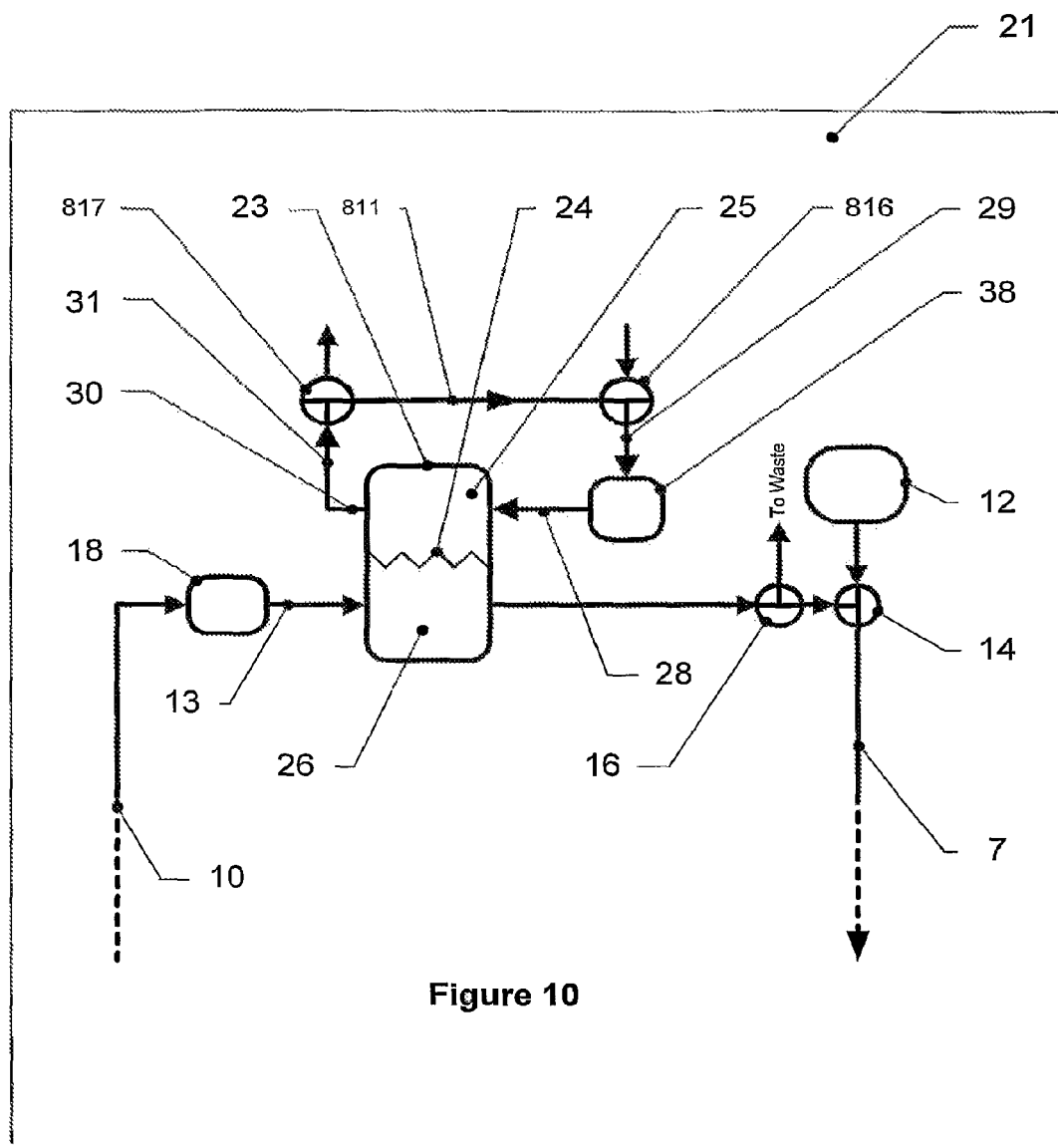

FIG. 10 is a schematic view of an apparatus for aspirating, irrigating and/or cleansing a wound according to the first aspect of the present invention. It has a two-phase system means for fluid cleansing in the form of a dialysis unit, or a biphasic extraction unit.

DETAILED DESCRIPTION OF THE PREFERRED EMBODIMENT

Figure 1A:
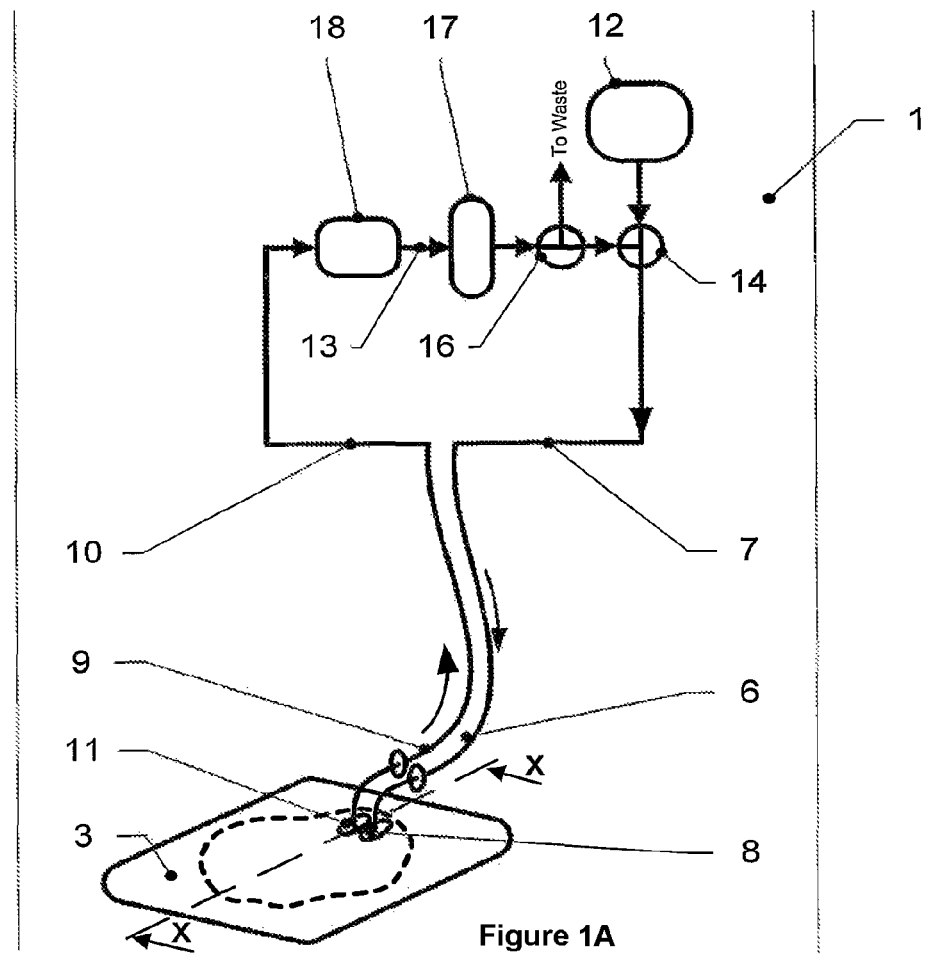
FIG. 1a is a schematic view of an apparatus for aspirating, irrigating and/or cleansing a wound according to the first aspect of the present invention.
Figure 1B:
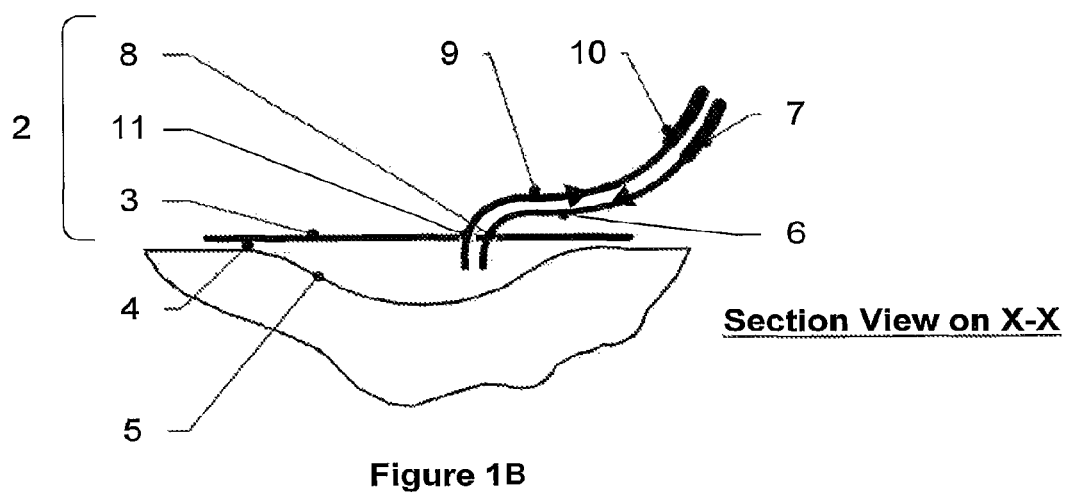

Referring to FIGS. 1a and 1b, the apparatus (1) for aspirating, irrigating and/or cleansing wounds comprises a conformable wound dressing (2), having a backing layer (3) which is capable of forming a relatively fluid-tight seal or closure (4) over a wound (5) and one inlet pipe (6) for connection to a fluid supply tube (7), which passes through the wound-facing face of the backing layer (3) at (8), and one outlet pipe (9) for connection to a fluid offtake tube (10), which passes through the wound-facing face at (11), the points (8), (11) at which the inlet pipe and the outlet pipe passes through and/or under the wound-facing face forming a relatively fluid-tight seal or closure over the wound, and means for stressing the wound in the form of a fluid-inflatable filler (111) (omitted for clarity) adapted to be inflated with air supplied through an inflation inlet pipe (150), mounted centrally and in passing through the backing layer (3) above the filler (111) from a small, portable diaphragm pump (151) with a bleed valve (116) by which air may be released from the filler (111), the inlet pipe is connected via means for flow switching between supply and recirculation, here a T-valve (14), by the fluid supply tube (7) to a fluid reservoir (12) and to a fluid recirculation tube (13) having a means for bleeding the tube, here a bleed T-valve (16) to waste, e.g. to a collection bag (not shown), the outlet pipe (9) being connected to a fluid offtake tube (10), connected in turn to means for fluid cleansing (17), here in the form of an ultrafiltration unit, connected to the inlet pipe (6) via the fluid recirculation tube (13) and T-valves (14) and (16) to a device for moving fluid through the wound and means for fluid cleansing (17), here a peristaltic pump (18), e.g. preferably a small portable peristaltic pump, acting on the fluid circulation tube (13) with the peripheral rollers on its rotor (not shown) to apply a low negative pressure on the wound.

The ultrafiltration unit (17) is a single-phase system.

In this the circulating fluid from the wound and the fluid reservoir passes through a self-contained system in which materials deleterious to wound healing are removed and the cleansed fluid, still containing materials that are beneficial in promoting wound healing, is returned via the recirculation tube to the wound bed.

(In a variant of this apparatus, there are two inlet pipes (6), which are connected respectively to a fluid supply tube (7) and fluid recirculation tube (13), respectively having a first valve (19) for admitting fluid into the wound from the fluid reservoir (12) and a second valve (20) for admitting fluid into the wound from the recirculation tube.

Usually in use of the apparatus, when the first valve (19) is open, the second valve (20) is shut, and vice versa.)

In use of the apparatus, if the inflation system bleed valve (116) by which air may be released from the filler (111) is open, it is then closed. The pump (151) is started to inflate the filler (111) with air through the inflation inlet pipe (150) towards the desired pressure on the wound bed.

The running of the pump (150) is continued until desired pressure is reached, and meanwhile the valve (16) is opened to a collection bag (not shown), and the T-valve (14) is turned to admit fluid from the fluid reservoir to the wound dressing through the fluid supply tube (7) and inlet pipe (6).

(In the variant of this apparatus having two inlet pipes (6), which are connected respectively to a fluid supply tube (7) and fluid recirculation tube (13), the first valve (19) for admitting fluid into the wound from the fluid reservoir (12) is opened and the second valve (20) is shut, and vice versa.)

The pump (18) is started to nip the fluid recirculation tube (13) with the peripheral rollers on its rotor (not shown) to apply a low positive pressure on the wound. It is allowed to run until the apparatus is primed throughout the whole length of the apparatus flow path and excess fluid is voided to waste via the bleed T-valve (16) into the collection bag (not shown).

The T-valve (14) is then turned to switch from supply and recirculation, i.e. is set to close the wound to the fluid reservoir (12) but to admit fluid into the wound from the fluid recirculation tube (13), and the bleed T-valve (16) is simultaneously closed.

(In the variant of this apparatus, where there are two inlet pipes (6), which are connected respectively to a fluid supply tube (7) and fluid recirculation tube (13), the first valve (19) is closed and a recirculating system set up by opening the second valve (20) for admitting fluid into the wound from the recirculation tube (13).

The circulating fluid from the wound and the fluid reservoir (12) passes through the ultrafiltration unit (17). Materials deleterious to wound healing are removed and the cleansed fluid, till containing materials that are beneficial in promoting wound healing, is returned via the recirculation tube (13) to the wound bed.

The recirculation of fluid may be continued as long as desired.

At any time after steady state recirculation has been achieved, the pressure on the wound bed and/or the fluid thereover may be varied, preferably cyclically, either randomly or regularly. This can be done by stopping the pump (151) and opening the closed inflation system bleed valve (116) so that air is released from the filler (111) to deflate it to a second desired pressure on the wound bed.

The inflation-deflation cycle may be continue as long as desired.

To stop the apparatus (1) switching between supply and recirculation is reversed, by turning the T-valve (14) to admit fluid from the fluid reservoir to the wound dressing through the fluid supply tube (7) and inlet pipe (6).

(In the variant of this apparatus having two inlet pipes (6), which are connected respectively to a fluid supply tube (7) and fluid recirculation tube (13), the first valve (19) for admitting fluid into the wound from the fluid reservoir (12) is opened and the second valve (20) is shut, and vice versa.) The bleed valve (16) is simultaneously opened, so that fresh fluid flushes the recirculating system.

The running of the pump (18) may be continued until the apparatus is flushed, when it and the fluid recirculation is stopped.

If, e.g. the wound is in a highly exuding state, there is a positive change in the balance of fluid in recirculation. It may be necessary to bleed fluid from recirculation, by opening the bleed T-valve (16) to bleed fluid from the recirculation tube (13).

Referring to FIG. 2, the apparatus (21) is a variant of that of FIG. 1*a*, with identical, and identically numbered, components, except for the means for fluid cleansing, which is in the form of a two-phase system, here a dialysis unit (23).

In this, there is one system through which the circulating fluid from the wound and the fluid reservoir passes and from which deleterious materials are removed by selectively permeable contact with a second system, through which passes a cleansing fluid.

The dialysis unit (23) thus has an internal polymer film, sheet or membrane (24), selectively permeable to materials deleterious to wound healing, which divides it into a) a first chamber (25), through which passes a cleansing fluid across one surface of the polymer film, sheet or membrane, and b) a second chamber (26), through which passes the circulating fluid from the wound and the fluid reservoir (12), and from which deleterious materials are removed The dialysis unit (23) thus has a dialysate inlet pipe (28) connecting to a dialysate supply tube (29) which passes to a peristaltic pump (38), e.g. preferably a small portable peristaltic pump, acting on the dialysate supply tube (29) with the peripheral rollers on its rotor (not shown).

This supplies cleansing fluid across the surface of the polymer film, sheet or membrane (24) in the first chamber (25) from a dialysate reservoir (not shown) via a valve (34).

The dialysis unit (23) also has a dialysate outlet pipe (30) connecting to a dialysate outlet tube (31) which passes to waste via a second bleed T-valve (36) into, e.g. a collection bag (not shown).

Operation of this apparatus is similar to that of FIG. 1*a*, except for the dialysis unit (23):

At some point after the irrigation system is primed and steady state recirculation established through the length of the apparatus flow path, the valve (34) and second bleed valve (36) are opened.

The pump (38) is started to nip fluid dialysate tube (29) with the peripheral rollers on its rotor (not shown) to pump cleansing fluid to the first chamber from a dialysate reservoir (not shown) and out to waste via the bleed valve (36) into the collection bag (not shown).

At any time after steady state recirculation has been achieved, the pressure on the wound bed and/or the fluid thereover may be varied, preferably cyclically, either randomly or regularly. This can be done by stopping the pump (151) and opening the closed inflation system bleed valve (116) so that air is released from the filler (111) to deflate it to a second desired pressure on the wound bed.

The inflation-deflation cycle may be continue as long as desired.

The dialysis unit (23) is a module (or scrubbing cartridge) with a substrate that changes colour to indicate the presence of detrimental factors in the cleansed fluid, and that the scrubbing cartridge is exhausted and should be renewed.

In a variant of the apparatus shown in FIG. 2, the dialysis unit has a first chamber (25), but one in which the cleansing fluid is static.

The device for moving fluid through the wound and means for fluid cleansing (23) in FIG. 2, a peristaltic pump (18), may optionally act on the fluid supply tube (7) as well as the fluid recirculation tube (13).

Referring to FIGS. 3a to 7, each dressing (41) is in the form of a conformable body defined by a microbe-impermeable film backing layer (42) with a uniform thickness of 25 micron, with a wound-facing face (43) which is capable of forming a relatively fluid-tight seal or closure over a wound.

The backing layer (42) extends in use on a wound over the skin around the wound. On the proximal face of the backing layer (43) on the overlap (44), it bears an adhesive film (45), to attach it to the skin sufficiently to hold the wound dressing in place in a fluid-tight seal around the periphery of the wound-facing face (43) of the wound dressing.

There is one inlet pipe (46) for connection to a fluid supply tube (not shown), which passes through and/or under the wound-facing face (43), and one outlet pipe (47) for connection to a fluid offtake tube (not shown), which passes through and/or under the wound-facing face (43).

Referring to FIGS. 3a and 3b, a more suitable form for shallower wounds is shown. This comprises a circular backing layer (42) and a circular upwardly dished first membrane (61) with apertures (62) that is permanently attached to the backing layer (42) by heat-sealing to form a circular pouch (63).

The pouch (63) communicates with the inlet pipe (46) through a hole (64), and thus effectively forms an inlet pipe manifold that delivers the circulating fluid directly to the wound when the dressing is in use.

An annular second membrane (65) with openings (66) is permanently attached to the backing layer (42) by heat-sealing to form an annular chamber (67) with the layer (42).

The chamber (67) communicates with the outlet pipe (47) through an orifice (68), and thus effectively forms an outlet pipe manifold that collects the fluid directly from the wound when the dressing is in use.

Referring to FIGS. 4a and 4b, a variant of the dressing of FIGS. 3a and 3b that is a more suitable form for deeper wounds is shown. This comprises a circular backing layer (42) and a filler (69), in the form of an inverted frustroconical, solid integer, here a resilient elastomeric foam, formed of a thermoplastic, or preferably a cross-linked plastics foam.

It is permanently attached to the backing layer (42), with an adhesive film (not shown) or by heat-sealing.

A circular upwardly dished sheet (70) lies under and conforms to, but is a separate structure, permanently unattached to, the backing layer (42) and the solid integer (69).

A circular upwardly dished first membrane (71) with apertures (72) is permanently attached to the sheet (70) by heat-sealing to form a circular pouch (73) with the sheet (70).

The pouch (73) communicates with the inlet pipe (46) through a hole (74), and thus effectively forms an inlet pipe manifold that delivers the circulating fluid directly to the wound when the dressing is in use.

An annular second membrane (75) with openings (76) is permanently attached to the sheet (70) by heat-sealing to form an annular chamber (77) with the sheet (70).

The chamber (77) communicates with the outlet pipe (77) through an orifice (78), and thus effectively forms an outlet pipe manifold that collects the fluid directly from the wound when the dressing is in use.

Alternatively, where appropriate the dressing may be provided in a form in which the circular upwardly dished sheet (70) functions as the backing layer and the solid filler (69) sits on the sheet (70) as the backing layer, rather than under it. The filler (69) is held in place with an adhesive film or tape, instead of the backing layer (42).

Figure 5B:
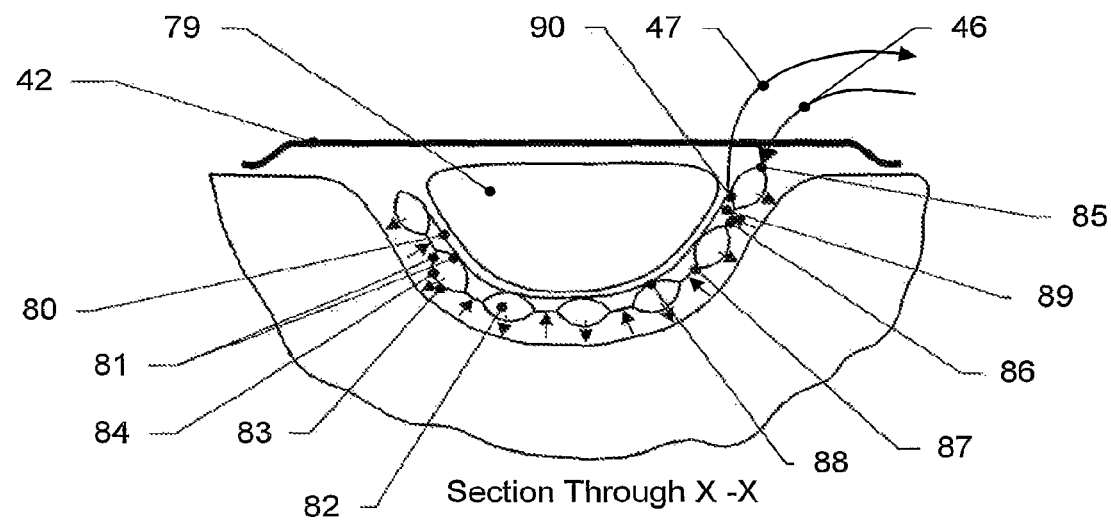

Referring to FIGS. 5a and 5b, a dressing that is a more suitable form for deeper wounds is shown.

This comprises a circular backing layer (42) and a filler (79), in the form of an inverted generally hemispherical integer, e.g. a resilient elastomeric foam or a hollow body filled with a fluid, e.g. a gel that urges it to the wound shape, and permanently unattached to the backing layer.

The inlet pipe (46) and outlet pipe (47) are mounted peripherally in the backing layer (42).

A circular upwardly dished sheet (80) lies under and conforms to, but is a separate structure, permanently unattached to, the backing layer (42) and the filler (79).

A circular upwardly dished bilaminate membrane (81) has a closed channel (82) between its laminar components, with
  perforations (83) along its length on the outer surface (84) of the dish formed by the membrane (81) and
  an opening (85) at the outer end of its spiral helix, through which the channel (82) communicates with the inlet pipe (46),
  and thus effectively forms an inlet pipe manifold that delivers the circulating fluid directly to the wound when the dressing is in use.

The membrane (81) also has apertures (86) between and along the length of the turns of the channel (82).

The inner surface (87) of the dish formed by the membrane (81) is permanently attached at its innermost points (88) with an adhesive film (not shown) or by heat-sealing to the sheet (80). This defines a mating closed spirohelical conduit (89).

At the outermost end of its spiral helix, the conduit (89) communicates through an opening (90) with the outlet pipe (47) and is thus effectively an outlet manifold to collect the fluid directly from the wound via the apertures (86).

Figure 6:
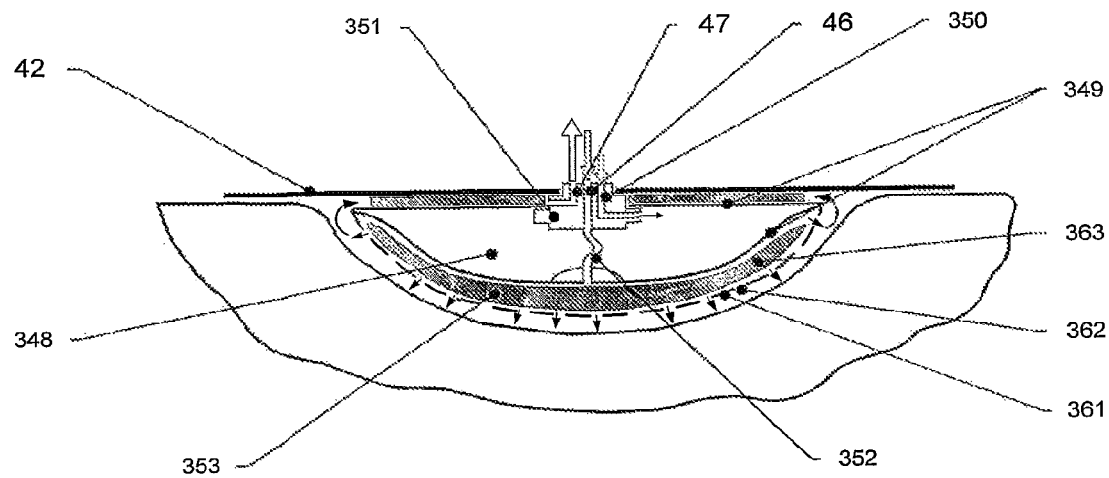
Figure 7:
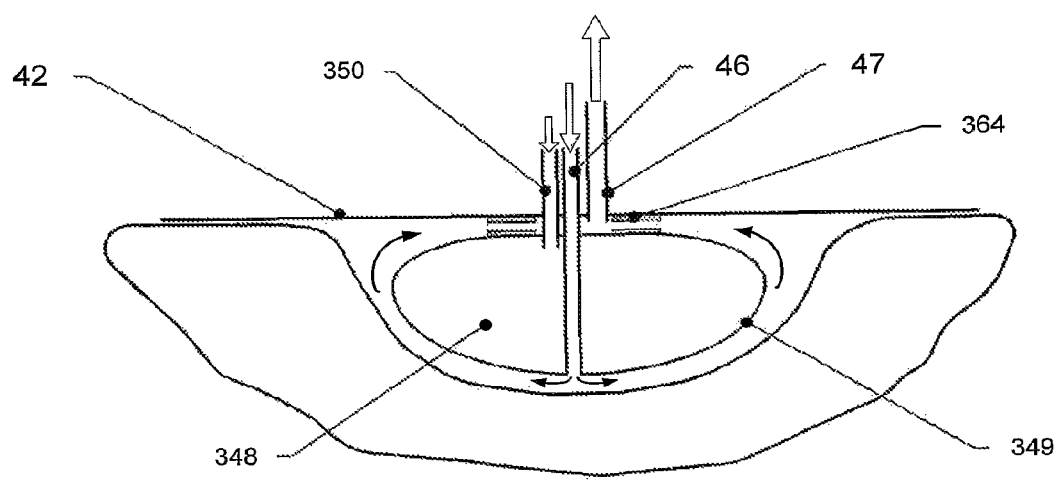

Referring to FIGS. 6 and 7, these forms of the dressing are provided with a wound filler (348) under a circular backing layer (42).

This comprises respectively a generally downwardly domed or oblately spheroidal conformable hollow body, defined by a membrane (349) which is filled with a fluid, here air or nitrogen, that urges it to the wound shape.

An inflation inlet pipe (350), inlet pipe (46) and outlet pipe (47) are mounted centrally in the boss (351) in the backing layer (42) above the hollow body (348). The inflation inlet pipe (350) communicates with the interior of the hollow body (348), to permit inflation of the body (348).

The inlet pipe (46) extends in a pipe (352) effectively through the hollow body (348). The outlet pipe (47) extends radially immediately under the backing layer (42).

In FIG. 6, the pipe (352) communicates with an inlet manifold (353), formed by a membrane (361) with apertures (362) that is permanently attached to the filler (348) by heat-sealing. It is filled with foam (363) formed of a suitable material, e.g. a resilient thermoplastic. Preferred materials include reticulated filtration polyurethane foams with small apertures or pores.

The filler (348) is permanently attached to the backing layer via a boss (351), which is e.g. heat-sealed to the backing layer (42).

In FIG. 7, the outlet pipe (47) communicates with a layer of foam (364) formed of a suitable material, e.g. a resilient thermoplastic. Again, preferred materials include reticulated filtration polyurethane foams with small apertures or pores.

In both of FIGS. 6 and 7, in use, the pipe (352) ends in one or more openings that deliver the irrigant fluid directly from the wound bed over an extended area.

Similarly, the outlet pipe (47) effectively collects the fluid radially from the wound periphery when the dressing is in use. This form of the dressing is a more suitable layout for deeper wounds.

Referring to FIG. 8a, another form for deeper wounds is shown. This comprises a circular, or more usually square or rectangular backing layer (342) and a chamber (363) in the form of a deeply indented disc much like a multiple Maltese cross or a stylised rose.

This is defined by an upper impervious membrane (361) and a lower porous film (362) with apertures (364) that deliver the irrigant fluid directly to the wound bed over an extended area, and thus effectively forms an inlet manifold. Three configurations of the chamber (363) are shown in FIG. 8b, all of which are able to conform well to the wound bed by the arms closing in and possibly overlapping in insertion into the wound.

The space above the chamber (363) is filled with a wound filler (348) under the backing layer (342). This comprises an oblately spheroidal conformable hollow body, defined by a membrane (349) that can be filled with a fluid, here air or nitrogen, that urges it to the wound shape. An inflation inlet pipe (350) is mounted centrally in a first boss (370) in the backing layer (342) above the hollow body (348). The inflation inlet pipe (350) communicates with the interior of the hollow body (348), to permit inflation of the body (348).

A moulded hat-shaped boss (351) is mounted centrally on the upper impervious membrane (361) of the chamber (363). It has three internal channels, conduits or passages through it (not shown), each with entry and exit apertures.

The filler (348) is attached to the membrane (361) of the chamber (363) by adhesive, heat welding or a mechanical fixator, such as a cooperating pin and socket.

An inflation inlet pipe (350), inlet pipe (346) and outlet pipe (347) pass under the edge of the proximal face of the backing layer (342) of the dressing.

They extend radially immediately under the filler (348) and over the membrane (361) of the chamber (363) to each mate with an entry aperture in the boss (351).

An exit to the internal channel, conduit or passage through it that receives the inflation inlet pipe (350) communicates with the interior of the hollow filler (348), to permit inflation.

An exit to the internal channel, conduit or passage that receives the inlet pipe (346) communicates with the interior of the chamber (363) to deliver the irrigant fluid via the chamber (363) to the wound bed over an extended area.

Similarly, an exit to the internal channel, conduit or passage that receives the outlet pipe (347) communicates with the space above the chamber (363) and under the wound filler (348), and collects flow of irrigant and/or wound exudate radially from the wound periphery.

Referring to FIGS. 9a and 9b, the apparatus (1) for aspirating, irrigating and/or cleansing wounds is a variant of the apparatus (1) of FIG. 1a.

It has bypass (711) around the pump (18), as a protection of the pump against any blockage in the system.

It is activated automatically by appropriate means, e.g. it is normally blocked by a bursting disc (not shown), or a pressure-activated motorised valve.

An alternative to the by-pass (711) is a pressure sensor in the system that will detect excessive load or pressure, and shut down the pump.

Referring to FIG. 10, the apparatus (1) for aspirating, irrigating and/or cleansing wounds is a variant of the apparatus (1) of FIG. 2.

The latter is a two-phase system with a dialysis unit (23), but is one in which dialytic fluid passes only once across the surface of the dialytic membrane (24) in the first chamber (25) from a dialysate reservoir (not shown) to waste via a second bleed T-valve (817) into, e.g. a collection bag (not shown).

This variant has a dialysate recirculation tube (811) running between a first T-valve (816) on the inlet side of the dialysate pump (38) and a second T-valve (817) to permit the pump (38) to recirculate the dialysate once the circuit is primed in multiple passes through the dialysis unit (23).

The operation of the system will be apparent to the skilled person.

The use of the apparatus of the present invention will now be described by way of example only in the following Examples:

Example 1

The Combination of the Removal by Dialysis of Materials Deleterious to Wound Healing ($H_2O_2$) by an Enzyme (Catalase) Retained in a Static Second Phase and Stress on Fibroblasts An apparatus of the present invention was constructed essentially as in the variant of the apparatus of FIG. 2, described above, i.e. one in which the means for fluid cleansing is a two-phase system dialysis unit. In such an apparatus, a) an irrigant and/or wound exudate first phase from the wound recirculates through a first circuit and passes over the dialysis unit in contact across a selectively permeable dialysis membrane with a second static fluid (dialysate) phase, and b) the peristaltic pump which is the device for moving fluid through the (surrogate) wound acts on the supply tube to and the offtake tube from the wound.

The means for stressing tissue representing a wound bed was a Flexercell® Tension Plus, FX-4000T, which is a computer-driven instrument that simulates biological strain conditions. It uses vacuum to deform and flex up and down, usually in a cyclical and regular manner, a flexible, matrix-bonded growth surface of BioFlex® or Flex® series culture plates, in multiple wells on which cells are cultured, thus subjecting the cell culture to strain.

Hydrogen peroxide is produced in conditions of oxidative stress following reduced blood flow and or the inflammatory response to bacterial contamination of wounds.

It may be removed by the appropriate antagonists and/or degraders, which include enzymic or other inhibitors, such as peroxide degraders, e.g. catalase.

Each first circuit comprised a well in a Bioflex plate (Flexercell International Corporation), a 6 well plate coated with laminin, with a silicone flexible base, in which normal diploid human fibroblasts were cultured. Each well containing cells representing the wound bed is a surrogate wound in the first circuit represented in the variant of FIG. 2 below.

Tissues present in the healing wound that must survive and proliferate are represented by the cells within the base of the well. Nutrient medium (DMEM with 10% FCS with 1% Buffer All) to simulate wound exudate was pumped from a reservoir into the well where it bathed the fibroblasts and was removed from the wells and returned to the reservoir.

A length of dialysis tubing (Pierce Snake skin 68100 CG 49358B, 10 KD cut off) was placed within the first circuit reservoir, in which was a second static cleansing phase containing nutrient media with between 5,000 and 50,000 units (µ moles $H_2O_2$ degraded per min at pH7, 25° C.) per ml of catalase (in a circuit with a reservoir and total volume of between 5.0 ml and 20 ml)

A cyclic tensile strain was applied to the underside of the Bioflex plate, resulting in a deformation of the silicone elastomer culture substrate. A strain value of 10% elongation was applied to the wells with a frequency of 6 cycles·min−1 (0.1 Hz), using a sine wave profile.

The pumps for the circuit are peristaltic acting on silicone elastic tubing or equivalent. The internal diameter of the tubing was 1.0 mm. A total volume for the first circuit including the chamber and the reservoir at a number of values between 70-75 ml was used. The flow rates used are 1.0 ml min$^{-1}$.

Experiments are conducted that simulated conditions not uncommon for non-healing wounds whereby the chamber simulating the wound contains nutrient medium containing a material deleterious to wound healing, namely hydrogen peroxide, was circulated over the cells.

First and second control apparatus are also constructed essentially as in variant of the apparatus of FIG. 2, described above, but where either a) the cleansing membrane dialysis unit is omitted, so that the nutrient flow passes directly from the reservoir, or b) the stress applied using Flexercell is omitted from the base of the plate so the fibroblasts are not stimulated.

In controls where either a) the passage of the nutrient flow past or through the cleansing membrane dialysis unit or b) stress applied using Flexercell is omitted and c) concentration of $H_2O_2$ lies between 5 and 20 mM and the temperature of the nutrient medium bathing the cells is between 18° C. and 20° C., activity and growth of the fibroblasts is not stimulated.

However, when the nutrient medium flow in the first circuit is a) passed over the membrane dialysis unit in which a second cleansing circuit containing catalase (at the concentrations and flow rates noted above) is present, and b) stress is applied using Flexercell delivering a cyclic tensile strain value of 10% elongation was applied with a frequency of 6 cycles·min−1 (0.1 Hz), using a sine wave profile.

the fibroblasts survive and proliferate to a greater extent during than the control circuits.

Results

The following results are obtained: A first phase of nutrient medium containing 10 µM $H_2O_2$ at a flow rate of 1.0 ml min$^{-1}$ with a 15 ml static second phase containing 7,600 units ml$^{-1}$ catalase contained within a length of dialysis tubing placed within the first circuit reservoir. The effect of the catalase cleansing unit and the Flexercell was as follows:

| Conditions | Mean level of cell activity after 24 hrs* (n = 3) |
|---|---|
| Normal media control | 100% |
| $H_2O_2$ in media | 60.4% |
| $H_2O_2$ in media with catalase second dialysis unit | 65.1% |
| Normal media plus Flexercell | 87.3% |
| $H_2O_2$ in media plus Flexercell | 44.3% |
| $H_2O_2$ in media with catalase second dialysis unit plus Flexercell | 111.9% |

*Cell activity measured with WST (Tetrazolium based mitochondrial dehydrogenase activity assay). All data was normalised against cells in fresh media only, subjected to flow only (represented as 100%).

Conclusions

The combination of the cleansing dialysis unit that removes and degrades $H_2O_2$ and the Flexercell unit enhances the cell response necessary for wound healing.

Example 2

The Combination of the Removal by Dialysis of Materials Deleterious to Wound Healing ($H_2O_2$) by an Enzyme (Catalase) Retained in a Moving Second Phase and in Combination with Stress An apparatus of the present invention is constructed essentially as in FIG. 2, i.e. one in which the means for fluid cleansing is a two-phase system dialysis unit. In such an apparatus, an irrigant and/or wound exudate first phase from the wound recirculates through a first circuit and passes in through the dialysis unit in contact across a selectively permeable dialysis membrane with a second fluid (dialysate) phase. The dialysis unit is operated with the two phases flowing counter-current to each other.

Hydrogen peroxide is produced in conditions of oxidative stress following reduced blood flow and or the inflammatory response to bacterial contamination of wounds. It may be removed by the appropriate antagonists and/or degraders, which include enzymic or other inhibitors, such as peroxide degraders, e.g. catalase.

Each first circuit comprises a well in a Bioflex plate (Flexercell International Corporation), a 6 well plate coated with laminin, with a silicone flexible base, in which normal diploid human fibroblasts were cultured. Each well containing cells representing the wound bed is a surrogate wound in the first circuit represented in FIG. 2 below.

Tissues present in the healing wound that must survive and proliferate are represented by the cells within the base of the well. Nutrient medium (DMEM with 10% FCS with 1% Buffer All) to simulate wound exudate is pumped from a reservoir into the wells where it bathed the fibroblasts and is removed from the wells and returned to the reservoir.

The first circuit also comprises upstream of the wound chamber, a luer-fitting hollow fibre tangential membrane dialysis unit (Spectrum® MicroKros® X14S-100-04N, 8 cm$^2$ surface area, 400 KD Mol. Wt. cut off,) with a second cleansing circuit.

Nutrient media with between 5,000 and 50,000 units (µ moles $H_2O_2$ degraded per min at pH7, 25° C.) per ml of catalase (in a circuit with a reservoir and total volume of between 5.0 ml and 20 ml) could be passed in a counter current direction through the second circuit at a flow rate of between 0.5 ml min$^{-1}$ and 5.0 ml min$^{-1}$.

A cyclic tensile strain (stress) is applied to the underside of the Bioflex plate, resulting in a deformation of the silicone elastomer culture substrate. A strain value of 10% elongation is applied to the wells with a frequency of 6 cycles·min−1 (0.1 Hz), using a sine wave profile.

The pumps for the two circuits are peristaltic pumps acting on silicone tubing or equivalent. The internal diameter of the tubing is 1.0 mm. A total volume for the first circuit including the chamber and the reservoir at a number of values between 25 and 75 ml is used. The flow rates used are at a number of values between 0.5 ml min$^{-1}$ and 5.0 ml min$^{-1}$.

Experiments are conducted that simulated conditions not uncommon for non-healing wounds whereby the nutrient medium containing a material deleterious to wound healing, namely hydrogen peroxide, is circulated over the cells.

First and second control apparatus are also constructed essentially as in FIG. 2, but where either
- a) the cleansing membrane dialysis unit is omitted, so that the nutrient flow passes directly from the reservoir, or
- b) the stress applied using Flexercell is omitted from to the base of the plate so the fibroblasts are not stimulated.

In controls where either
- a) the passage of the nutrient flow through the cleansing membrane dialysis unit or
- b) the stress applied using Flexercell is omitted from the base of the plate or
- c) the concentration of $H_2O_2$ lies between 5 and 20 mM, the activity and growth of the fibroblasts are not stimulated or inhibited over a 24 hour period.

However, when
- a) the nutrient medium flow in the first circuit is connected into the ends of the membrane dialysis unit through which a second cleansing circuit containing catalase (at the concentrations and flow rates noted above) is passing in a counter current direction, and
- b) the cells are subjected to the stress applied using Flexercell the fibroblasts survive and proliferate to a greater extent during a 24 hour period than the control circuits.

The invention claimed is:

1. An apparatus for administering negative pressure to a wound, comprising:
   a backing layer adapted to cover a wound and adapted to maintain negative pressure at the site of the wound;
   a vacuum pump; and
   a controller configured to control the vacuum pump to cause the vacuum pump to apply a cyclically varying negative pressure under the backing layer, the cyclically varying negative pressure comprising first and second maximum amplitudes of negative pressure, the first maximum amplitude different from the second maximum amplitude;
   wherein the vacuum pump is configured to cooperate with the backing layer to supply the cyclically varying negative pressure under the backing layer to the wound; and
   wherein the cyclically varying negative pressure is below or above atmospheric pressure;
   wherein the cyclically varying negative pressure is one of a sinusoidal-waveform and a sawtooth-waveform.

2. The apparatus of claim 1, wherein a maximum vacuum level of the cyclically varying negative pressure is 15% atm below atmospheric pressure.

3. The apparatus of claim 1, further comprising a filler configured for placement at the wound between the backing layer and the wound.

4. The apparatus of claim 3, wherein the filler is configured to promote cell proliferation.

5. An apparatus for administering negative pressure to a wound, comprising:
   a negative pressure source configured to be fluidically connected to a wound dressing placed over a wound; and
   a controller configured to control the negative pressure source, the controller further configured to cause provision of a cyclically varying pressure under the wound dressing in accordance with a sinusoidal waveform between first and second maximum amplitudes of pressure, the first maximum amplitude different from the second maximum amplitude;
   wherein the sinusoidal waveform varies relative to a baseline pressure; and
   wherein the cyclically varying pressure is below or above atmospheric pressure.

6. The apparatus of claim 5, wherein the controller is further configured to cause provision of the cyclically varying pressure at at least one of: constant positive or negative baseline pressure, the baseline pressure varying below atmospheric pressure, the baseline pressure varying above atmospheric pressure, the baseline pressure varying between pressures below and above atmospheric pressure.

7. The apparatus of claim 5, wherein the first and second maximum amplitudes of pressure are below atmospheric pressure.

8. The apparatus of claim 5, wherein the first maximum amplitude of pressure is above atmospheric pressure and the second maximum amplitude of pressure is below atmospheric pressure.

9. The apparatus of claim 5, wherein the controller is further configured to cause provision of a cyclically varying positive and negative pressure.

10. The apparatus of claim 5, wherein the provision of the cyclically varying pressure is further configured to stress the wound.

11. The apparatus of claim 5, wherein the controller is further configured to cause the provision of the cyclically varying pressure at a controlled frequency.

12. The apparatus of claim 5, wherein the wound dressing comprises a conformable wound dressing configured to at least partially cover the wound, the wound dressing configured to form at least a relatively fluid tight seal around at least a portion of the wound.

13. The apparatus of claim 5, further comprising a wound filler configured to be positioned adjacent to the wound.

14. The apparatus of claim 5, further comprising:
   an inlet conduit configured to be in fluidic communication with the wound dressing; and
   an outlet conduit configured to be in fluidic communication with the wound dressing;
   wherein the controller is further configured to cause the negative pressure source to pump fluid through at least the inlet conduit, the wound dressing, and the outlet conduit.

15. The apparatus of claim 14, further comprising a cleansing mechanism configured to cleanse the fluid that flows out of the wound dressing to reduce the amount of deleterious components in the fluid that flows out of the dressing without substantially reducing the amount of the components in the fluid that flows out of the dressing that are beneficial to wound healing.

16. The apparatus of claim 15, wherein the cleansing mechanism comprises a fluid recirculation conduit configured to recirculate at least a portion of the fluid that flows out of the wound dressing back to the dressing after being cleansed so that nutrients, molecules, factors, and/or other components from the wound exudate that aid in proliferation or that are favorable to the wound healing process are returned to the wound.

17. An apparatus for administering negative pressure to a wound, comprising:
a negative pressure source configured to be fluidically connected to a wound dressing placed over a wound; and
a controller configured to control the negative pressure source to cause the provision of a varying pressure under the wound dressing in accordance with a waveform applied at a controlled frequency, the waveform varying relative to a baseline pressure and further varying between first and second maximum pressure values, the first maximum pressure value different from the second maximum pressure value, and at least one of the first or second maximum pressure values being below atmospheric pressure.

18. The apparatus of claim 17, wherein the waveform comprises at least one of: a sinusoidal waveform, random white noise waveform, sawtooth waveform, or square waveform.

19. The apparatus of claim 17, wherein the first and second maximum pressure values are below atmospheric pressure.

20. The apparatus of claim 17, wherein the varying pressure comprises at least one of: a constant positive or negative baseline pressure, varying baseline pressure below atmospheric pressure, varying baseline pressure above atmospheric pressure, or varying baseline pressure below and above atmospheric pressure.

21. The apparatus of claim 17, wherein the first maximum pressure value is below atmospheric pressure and the second maximum pressure values is above atmospheric pressure.

22. The apparatus of claim 17, wherein the first and second maximum pressure values are below atmospheric pressure.

23. The apparatus of claim 17, wherein the waveform is a sinusoidal waveform.

24. The apparatus of claim 17, wherein the waveform is a systolic-diastolic asymmetric sawtooth waveform configured to stress the wound, and wherein the first maximum pressure values are below atmospheric pressure and the second maximum pressure values are above atmospheric pressure.

25. The apparatus of claim 17, wherein the provision of the varying negative pressure further comprises stressing the wound.

26. The apparatus of claim 17, wherein the controlled frequency is between 1 and 3000 cycles per minute.

27. The apparatus of claim 17, wherein the wound dressing comprises a conformable wound dressing configured to at least partially cover the wound, the wound dressing configured to form at least a relatively fluid tight seal around at least a portion of the wound.

28. The apparatus of claim 17, further comprising a wound filler configured to be positioned adjacent to the wound.

* * * * *

UNITED STATES PATENT AND TRADEMARK OFFICE
CERTIFICATE OF CORRECTION

PATENT NO.         : 9,526,817 B2
APPLICATION NO.    : 14/184643
DATED              : December 27, 2016
INVENTOR(S)        : Patrick Lewis Blott Page 1 of 2

It is certified that error appears in the above-identified patent and that said Letters Patent is hereby corrected as shown below:

Page 1 (item (57), Abstract) at Line 6, Change "devise" to --device--.

In Column 2 (page 3, item (56)) at Line 41, Under Other Publications, change "salmoncida:" to --salmonicida:--.

In Column 2 (page 3, item (56)) at Line 61, Under Other Publications, change "Majdanepek," to --Majdanpek,--.

In Column 3 at Line 30, Before "at" delete "and".

In Column 5 at Line 17, Change "than" to --then--.

In Column 9 at Line 23, Change "pump." to --pump;--.

In Column 9 at Line 29 (approx.), Change "pump." to --pump;--.

In Column 13 at Line 38, Change "the" to --they--.

In Column 15 at Line 9, After "bed" insert --.--.

In Column 20 at Line 29, Change "xylocalne (adrenoline," to --xylocaine (adrenaline,--.

In Column 22 at Line 14 (approx.), Change "flow." to --flow;--.

In Column 22 at Line 22, Change "housing." to --housing;--.

In Column 22 at Line 30 (approx.), Change "pump." to --pump;--.

In Column 25 at Line 17 (approx.), After "materials" insert --.--.

Signed and Sealed this
Eighteenth Day of April, 2017

Michelle K. Lee
*Director of the United States Patent and Trademark Office*

CERTIFICATE OF CORRECTION (continued)
U.S. Pat. No. 9,526,817 B2

In Column 26 at Line 32, Change "(IL-β)," to --(IL-1β),--.

In Column 27 at Line 52, Change "xylocalne (adrenoline" to --xylocaine (adrenaline,--.

In Column 28 at Line 25, After "peptidomimetics" insert --.--.

In Column 29 at Line 59, Change "(IL-β);" to --(IL-1β);--.

In Column 36 at Line 31, After "removed" insert --.--.

In Column 37 at Lines 47-48 (approx.), Change "frustroconical," to --frustoconical,--.

In Column 40 at Line 57, Change "and or" to --and/or--.

In Column 41 at Line 13 (approx.), After "ml)" insert --.--.

In Column 42 at Line 12 (approx.), Change "dehdrogenase" to --dehydrogenase--.

In Column 42 at Line 14 (approx.), Change "100%) ." to --100%).--.

In Column 42 at Line 37, Change "and or" to --and/or--.